US011235131B2

(12) United States Patent
Degen et al.

(10) Patent No.: US 11,235,131 B2
(45) Date of Patent: *Feb. 1, 2022

(54) APPARATUS AND METHODS FOR TREATING INTRACORPOREAL FLUID ACCUMULATION

(71) Applicants: Sequana Medical NV, Zwijnaarde (BE); Lorraine Johnson

(72) Inventors: Thomas Werner Degen, Birmensdorf (CH); Daniel Thomas Thommen, Steinhausen (CH); Noel L. Johnson, Saratoga, CA (US)

(73) Assignee: Sequana Medical NV, Zwijnaarde (BE)

( * ) Notice: Subject to any disclaimer, the term of this patent is extended or adjusted under 35 U.S.C. 154(b) by 477 days.

This patent is subject to a terminal disclaimer.

(21) Appl. No.: 16/378,376

(22) Filed: Apr. 8, 2019

(65) Prior Publication Data
US 2019/0232029 A1    Aug. 1, 2019

Related U.S. Application Data

(63) Continuation of application No. 14/874,187, filed on Oct. 2, 2015, now Pat. No. 10,252,037, which is a
(Continued)

(51) Int. Cl.
*A61M 1/28* (2006.01)
*A61M 27/00* (2006.01)
(Continued)

(52) U.S. Cl.
CPC ............ *A61M 27/002* (2013.01); *A61M 1/28* (2013.01); *A61M 5/14236* (2013.01);
(Continued)

(58) Field of Classification Search
CPC ....... A61B 17/02; A61B 17/08; A61F 5/4404; A61F 5/4408; A61F 5/445; A61F 5/449;
(Continued)

(56) References Cited

U.S. PATENT DOCUMENTS 3,540,451 A    11/1970 Zenman
3,575,158 A     4/1971 Summers
(Continued)

FOREIGN PATENT DOCUMENTS

CN    101485683 A    7/2009
CN    201930383 U    8/2011
(Continued)

OTHER PUBLICATIONS

Bellot, Pablo, et al., Automated low flow pump system for the treatment of refractory ascites: A multi-center safety and efficacy study, Journal of Hepatology, 58(5):922-927 (2013).
(Continued)

*Primary Examiner* — Kai H Weng
(74) *Attorney, Agent, or Firm* — Eversheds Sutherland (US) LLP; Christopher C. Bolten; Nicola A. Pisano

(57) ABSTRACT

A fluid management system for the treatment of ascites, pleural effusion or pericardial effusion is provided including an implantable device including a pump, control circuitry, battery and transceiver; a charging and communication system configured to periodically charge the battery and communicate with the implantable device to retrieve performance data; and monitoring and control software, suitable for use with conventional personal computers, for configuring and controlling operation of the implantable device and charging and communication system. The implantable device includes a number of features that provide automated movement of fluid to the bladder with reduced risk of clogging, with no patient involvement other than occasional recharging of the battery of the implantable device. The monitoring and control software is available only to the treating physician, such that the physician interacts with the implantable device via the charging and communication system.

19 Claims, 9 Drawing Sheets

Related U.S. Application Data continuation of application No. 13/397,509, filed on Feb. 15, 2012, now Pat. No. 9,149,613.

(60) Provisional application No. 61/443,668, filed on Feb. 16, 2011.

(51) Int. Cl.
*A61M 5/142* (2006.01)
*G16H 40/63* (2018.01)
*G16H 20/17* (2018.01)

(52) U.S. Cl.
CPC ........ *A61M 5/14276* (2013.01); *G16H 40/63* (2018.01); *A61M 2205/10* (2013.01); *A61M 2205/3368* (2013.01); *A61M 2205/3379* (2013.01); *A61M 2205/3507* (2013.01); *A61M 2205/3569* (2013.01); *A61M 2205/502* (2013.01); *A61M 2205/52* (2013.01); *A61M 2205/8243* (2013.01); *A61M 2230/005* (2013.01); *A61M 2230/42* (2013.01); *G16H 20/17* (2018.01)

(58) Field of Classification Search
CPC ................ A61M 1/28; A61M 2205/10; A61M 2205/3379; A61M 2205/3507; A61M 2205/3569; A61M 2205/502; A61M 2205/52; A61M 2230/005; A61M 2230/42; A61M 27/002; A61M 5/14236; A61M 5/14276; G16H 40/63
See application file for complete search history.

(56) References Cited

U.S. PATENT DOCUMENTS

| | | |
|---|---|---|
| 3,654,932 A | 4/1972 | Newkirk et al. |
| 3,810,259 A | 5/1974 | Summers |
| 3,910,283 A | 10/1975 | Leveen |
| 4,014,346 A | 3/1977 | Brownlee et al. |
| 4,083,786 A | 4/1978 | Tsuda et al. |
| 4,240,434 A | 12/1980 | Newkirk |
| 4,261,341 A | 4/1981 | Hakim et al. |
| 4,354,933 A | 10/1982 | Lester |
| 4,416,657 A | 11/1983 | Berglund |
| 4,419,094 A | 12/1983 | Patel |
| 4,475,898 A | 10/1984 | Brodner et al. |
| 4,475,899 A | 10/1984 | Muller |
| 4,490,137 A | 12/1984 | Moukheibir |
| 4,553,956 A | 11/1985 | Muller |
| 4,610,625 A | 9/1986 | Bunn |
| 4,610,658 A | 9/1986 | Buchwald et al. |
| 4,615,691 A | 10/1986 | Hakim et al. |
| 4,618,343 A | 10/1986 | Polaschegg |
| 4,632,435 A | 12/1986 | Polyak |
| 4,657,530 A | 4/1987 | Buchwald et al. |
| 4,687,471 A | 8/1987 | Twardowski et al. |
| 4,725,207 A | 2/1988 | Buchwald et al. |
| 4,772,257 A | 9/1988 | Hakim et al. |
| 4,779,614 A | 10/1988 | Moise |
| 4,784,638 A | 11/1988 | Ghajar et al. |
| 4,850,955 A | 7/1989 | Newkirk et al. |
| 4,880,414 A | 11/1989 | Whipple |
| 4,904,236 A | 2/1990 | Redmont et al. |
| 4,963,129 A | 10/1990 | Rusch |
| 4,963,133 A | 10/1990 | Whipple |
| 5,011,472 A | 4/1991 | Aebischer et al. |
| 5,021,048 A | 6/1991 | Buckholtz |
| 5,037,385 A | 8/1991 | O'Byrne |
| 5,057,075 A | 10/1991 | Moncrief et al. |
| 5,071,408 A | 12/1991 | Ahmed et al. |
| 5,078,688 A | 1/1992 | Lobodzinski et al. |
| 5,147,281 A | 9/1992 | Thornton et al. |
| 5,167,615 A | 12/1992 | East et al. |
| 5,180,387 A | 1/1993 | Ghajar et al. |
| 5,254,084 A | 10/1993 | Geary |
| 5,356,386 A | 10/1994 | Goldberg et al. |
| 5,385,541 A | 1/1995 | Kirsch et al. |
| 5,387,188 A | 2/1995 | Watson |
| 5,387,192 A | 2/1995 | Glantz et al. |
| 5,391,143 A | 2/1995 | Kensey |
| 5,395,350 A | 3/1995 | Summers |
| 5,397,354 A | 3/1995 | Wilk et al. |
| 5,472,323 A | 12/1995 | Hirabayashi et al. |
| 5,474,683 A | 12/1995 | Bryant et al. |
| 5,575,770 A | 11/1996 | Melsky et al. |
| 5,589,197 A | 12/1996 | Shockley et al. |
| 5,629,025 A | 5/1997 | Shockley et al. |
| 5,631,025 A | 5/1997 | Shockley et al. |
| 5,637,083 A | 6/1997 | Bertrand et al. |
| 5,725,506 A | 3/1998 | Freeman et al. |
| 5,830,172 A | 11/1998 | Leveen et al. |
| 5,902,336 A | 5/1999 | Mishkin |
| 5,944,684 A | 8/1999 | Roberts et al. |
| 5,947,911 A | 9/1999 | Wong et al. |
| 5,980,478 A | 11/1999 | Gorsuch et al. |
| 5,989,207 A | 11/1999 | Hughes |
| 6,007,511 A | 12/1999 | Prywes |
| 6,017,355 A | 1/2000 | Hessel et al. |
| D420,738 S | 2/2000 | Carter et al. |
| 6,022,333 A | 2/2000 | Kensey |
| 6,132,405 A | 10/2000 | Nilsson et al. |
| 6,132,415 A | 10/2000 | Finch et al. |
| 6,162,238 A | 12/2000 | Kaplan et al. |
| 6,162,487 A | 12/2000 | Darouiche |
| 6,193,684 B1 | 2/2001 | Burbank et al. |
| 6,214,802 B1 | 4/2001 | Nakamura et al. |
| 6,245,039 B1 | 6/2001 | Brugger et al. |
| 6,248,726 B1 | 6/2001 | Alsop et al. |
| 6,254,567 B1 | 7/2001 | Treu et al. |
| 6,264,601 B1 | 7/2001 | Jassawalla et al. |
| 6,264,625 B1 | 7/2001 | Rubenstein et al. |
| 6,417,750 B1 | 7/2002 | Sohn |
| 6,436,087 B1 | 8/2002 | Lewis et al. |
| 6,533,733 B1 | 3/2003 | Ericson et al. |
| 6,554,822 B1 | 4/2003 | Holschneider et al. |
| 6,585,681 B2 | 7/2003 | Brugger et al. |
| 6,613,095 B1 | 9/2003 | Levin |
| 6,656,227 B2 | 12/2003 | Levin |
| 6,689,085 B1 | 2/2004 | Rubenstein et al. |
| 6,814,547 B2 | 11/2004 | Childers et al. |
| 6,827,682 B2 | 12/2004 | Bugge et al. |
| 6,845,267 B2 | 1/2005 | Harrison et al. |
| 6,846,168 B2 | 1/2005 | Davis et al. |
| 6,854,467 B2 | 2/2005 | Boekstegers |
| 6,875,192 B1 | 4/2005 | Saul et al. |
| 6,887,214 B1 | 5/2005 | Levin et al. |
| 6,894,456 B2 | 5/2005 | Tsukamoto et al. |
| 6,905,474 B2 | 6/2005 | Borgesen |
| 6,911,014 B2 | 6/2005 | Wentling et al. |
| 6,921,378 B2 | 7/2005 | O'Keefe et al. |
| 6,926,691 B2 | 8/2005 | Miethke |
| 6,939,111 B2 | 9/2005 | Huitt et al. |
| 6,945,949 B2 | 9/2005 | Wilk |
| 6,949,080 B2 | 9/2005 | Wolf et al. |
| 6,953,481 B2 | 10/2005 | Phelps et al. |
| 6,955,655 B2 | 10/2005 | Burbank et al. |
| 6,960,179 B2 | 11/2005 | Gura |
| 6,964,652 B2 | 11/2005 | Guiles et al. |
| 6,974,445 B2 | 12/2005 | Stergiopulos |
| 6,976,973 B1 | 12/2005 | Ruddell et al. |
| 6,979,351 B2 | 12/2005 | Forsell et al. |
| 6,981,964 B2 | 1/2006 | Rioux et al. |
| 6,994,700 B2 | 2/2006 | Elkins et al. |
| 7,011,095 B2 | 3/2006 | Wolf et al. |
| 7,017,340 B2 | 3/2006 | Chicky |
| 7,025,739 B2 | 4/2006 | Saul |
| 7,025,742 B2 | 4/2006 | Rubenstein et al. |
| 7,063,679 B2 | 6/2006 | Maguire et al. |
| 7,169,303 B2 | 1/2007 | Sullivan et al. |
| 7,195,608 B2 | 3/2007 | Burnett |
| 7,311,690 B2 | 12/2007 | Burnett |
| 7,335,179 B2 | 2/2008 | Burnett |
| 7,621,886 B2 | 11/2009 | Burnett |

(56) References Cited

U.S. PATENT DOCUMENTS

| | | |
|---|---|---|
| 7,670,332 B2 | 3/2010 | O'Keefe et al. |
| 7,909,790 B2 | 3/2011 | Burnett |
| 8,012,118 B2 | 9/2011 | Curtin et al. |
| 8,202,248 B2 | 6/2012 | Burnett et al. |
| 8,241,239 B2 | 8/2012 | Solomon et al. |
| 8,394,048 B2 | 3/2013 | Burnett |
| 8,398,577 B2 | 3/2013 | Burnett |
| 8,517,973 B2 | 8/2013 | Burnett |
| 8,585,635 B2 | 11/2013 | Degen et al. |
| 8,641,659 B2 | 2/2014 | Soykan et al. |
| 8,771,221 B2 | 7/2014 | Burnett |
| 8,882,699 B2 | 11/2014 | Burnett |
| 8,961,448 B2 | 2/2015 | Forsell |
| 8,992,456 B1 | 3/2015 | Powell |
| 9,039,652 B2 | 5/2015 | Degen et al. |
| 9,138,523 B2 | 9/2015 | Burnett et al. |
| 9,144,660 B2 | 9/2015 | Degen |
| 9,149,613 B2 | 10/2015 | Degen et al. |
| D743,542 S | 11/2015 | Degen |
| D743,543 S | 11/2015 | Degen |
| 9,339,636 B1 | 5/2016 | Khan et al. |
| 9,381,301 B2 | 7/2016 | Lattanzio et al. |
| 9,421,347 B2 | 8/2016 | Burnett |
| 9,577,459 B2 | 2/2017 | Degen et al. |
| 9,675,327 B2 | 6/2017 | Johnson et al. |
| 9,913,968 B2 | 3/2018 | Burnett |
| 9,956,336 B2 | 5/2018 | Degen et al. |
| 2002/0013545 A1 | 1/2002 | Soltanpour et al. |
| 2002/0022793 A1 | 2/2002 | Bertrand et al. |
| 2002/0123715 A1 | 9/2002 | Sorenson et al. |
| 2003/0114787 A1 | 6/2003 | Gura |
| 2003/0163079 A1 | 8/2003 | Burnett |
| 2003/0171710 A1 | 9/2003 | Bassuk et al. |
| 2003/0217962 A1 | 11/2003 | Childers et al. |
| 2003/0220606 A1 | 11/2003 | Busby et al. |
| 2004/0018228 A1 | 1/2004 | Fischell et al. |
| 2004/0049288 A1 | 3/2004 | Levin |
| 2004/0098113 A1 | 5/2004 | Forsell et al. |
| 2004/0126775 A1 | 7/2004 | Altieri et al. |
| 2004/0147871 A1 | 7/2004 | Burnett |
| 2005/0131340 A1 | 6/2005 | Sorenson et al. |
| 2005/0273034 A1 | 12/2005 | Burnett |
| 2006/0010014 A1 | 1/2006 | Brown |
| 2006/0024200 A1 | 2/2006 | Nishikiori et al. |
| 2006/0036208 A1 | 2/2006 | Burnett |
| 2006/0058731 A1 | 3/2006 | Burnett et al. |
| 2006/0094984 A1 | 5/2006 | Wood et al. |
| 2007/0055197 A1 | 3/2007 | Shakir |
| 2007/0106205 A1 | 5/2007 | Connell et al. |
| 2007/0228071 A1 | 10/2007 | Kamen et al. |
| 2007/0255345 A1 | 11/2007 | Krause |
| 2007/0299317 A1 | 12/2007 | Hoyme et al. |
| 2008/0108935 A1 | 5/2008 | Nyhart, Jr. |
| 2008/0154173 A1 | 6/2008 | Burnett |
| 2008/0214983 A1 | 9/2008 | Mauge et al. |
| 2008/0230450 A1 | 9/2008 | Burbank et al. |
| 2009/0069642 A1 | 3/2009 | Gao et al. |
| 2009/0171241 A1 | 7/2009 | Garcia et al. |
| 2009/0198174 A1 | 8/2009 | Childers et al. |
| 2009/0275924 A1 | 11/2009 | Lattanzio et al. |
| 2009/0318844 A1 | 12/2009 | Burnett |
| 2010/0010832 A1 | 1/2010 | Boute et al. |
| 2010/0114012 A1 | 5/2010 | Sandford et al. |
| 2010/0215375 A1 | 8/2010 | Reams |
| 2010/0249692 A1 | 9/2010 | Dacey et al. |
| 2010/0312163 A1 | 12/2010 | Forsell |
| 2010/0312164 A1 | 12/2010 | Forsell |
| 2011/0025261 A1 | 2/2011 | Bersenev |
| 2011/0034986 A1 | 2/2011 | Chou et al. |
| 2011/0184339 A1 | 7/2011 | Tan |
| 2011/0184340 A1 | 7/2011 | Tan et al. |
| 2012/0209085 A1 | 8/2012 | Degen et al. |
| 2012/0209165 A1 | 8/2012 | Degen et al. |
| 2013/0199998 A1 | 8/2013 | Kelly et al. |
| 2013/0211322 A1 | 8/2013 | Degen et al. |
| 2013/0289334 A1 | 10/2013 | Badstibner et al. |
| 2014/0012180 A1 | 1/2014 | Levin et al. |
| 2014/0066841 A1 | 3/2014 | Degen et al. |
| 2016/0000984 A1 | 1/2016 | Burnett et al. |
| 2016/0022971 A1 | 1/2016 | Degen et al. |
| 2016/0331947 A1 | 11/2016 | Burnett |
| 2017/0128654 A1 | 5/2017 | Feld |
| 2017/0281848 A1 | 10/2017 | Axelsson et al. |
| 2018/0056050 A1 | 3/2018 | Degen et al. |
| 2018/0060520 A1 | 3/2018 | Degen et al. |
| 2018/0243495 A1 | 8/2018 | Degen et al. |
| 2018/0338914 A1 | 11/2018 | Inhaber et al. |
| 2018/0344917 A1 | 12/2018 | Inhaber et al. |

FOREIGN PATENT DOCUMENTS

| | | |
|---|---|---|
| EP | 0 366 389 A2 | 5/1990 |
| EP | 0 980 685 | 2/2000 |
| EP | 1 362 605 A1 | 11/2003 |
| EP | 1 517 718 B1 | 3/2005 |
| EP | 1 539 294 B1 | 6/2005 |
| EP | 2 244 667 A1 | 11/2010 |
| EP | 2 676 638 B1 | 12/2013 |
| GB | 2 350 794 A | 12/2000 |
| JP | H04-327857 | 11/1992 |
| JP | A2004-513681 | 5/2004 |
| JP | A2005-171892 | 6/2005 |
| WO | WO-97/41799 A1 | 11/1997 |
| WO | WO-98/16171 A1 | 4/1998 |
| WO | WO-99/34116 A1 | 7/1999 |
| WO | WO-02/07596 A1 | 1/2002 |
| WO | WO-03/072166 A1 | 9/2003 |
| WO | WO-2004/012806 A1 | 2/2004 |
| WO | WO-2004/105730 A1 | 12/2004 |
| WO | WO-2005/018708 A1 | 3/2005 |
| WO | WO-2006/023589 A2 | 3/2006 |
| WO | WO-2008/055248 A1 | 5/2008 |
| WO | WO-2009/096854 A1 | 8/2009 |
| WO | WO-2010/077851 A2 | 7/2010 |
| WO | WO-201 2/112664 A1 | 8/2012 |
| WO | WO-201 3/122580 A1 | 8/2013 |
| WO | WO-201 3/166038 A2 | 11/2013 |
| WO | WO-201 4/140277 A1 | 9/2014 |
| WO | WO-201 5/108782 A1 | 7/2015 |
| WO | WO-201 8/037359 A1 | 3/2018 |

OTHER PUBLICATIONS

Costanzo et al., "Early Ultrafiltration in Patients with Decompensated Heart Failure and Diuretic Resistance," J. Am. Coll. Cardiol., (2005), vol. 46(11):2047-2051.

Doty, et al., Effect of Increased Renal Venous Pressure On Renal Function, J. Trauma., 47(6):1000-3 (1999).

Francois, et al., Peritoneal Dialysis For Chronic Congestive Heart Failure, Blood Purif., 40(1):45-52 (2015).

Fukuda, et al., Survivin, a cancer target with an emerging role in normal adult tissues, Mol. Cancer Ther., 5(5):1087-1098 (2006).

Hecking, et al., Sodium Setpoint and Sodium Gradient: Influence on Plasma Sodium Change And Weight Gain, Am J. Nephrol, 33(1):39-48 (2011).

Houlberg et al., "Terminal Right Heart Failure Due to Complex Congenital Cardiac Disease Successfully Managed by Home Peritoneal Drainage," Cardiol. Young, 13(6):568-70.

International Search Report & Written Opinion dated Jan. 4, 2018 in Int'l PCT Patent Appl. Serial No. PCT/IB2017/055092.

International Search Report & Written Opinion dated Mar. 18, 2013 in Int'l PCT Appl. No. PCT/US2012/025188.

International Search Report and Written Opinion dated Feb. 2, 2018 in Int'l PCT Patent Appl. No. PCT/IB2017/055093.

International Search Report and Written Opinion dated Apr. 16, 2015 in Int'l PCT Patent Appl. No. PCT/US2015/010840.

International Preliminary Report on Patentability dated May 16, 2014 in related Int'l PCT Patent Appl. No. PCT/US2012/025188.

International Search Report & Written Opinion dated Aug. 24, 2018 in Int'l PCT Patent Appl. Serial No. PCT/IB2018/053587.

(56) References Cited

OTHER PUBLICATIONS

Invitation to Pay Additional Fees and Communication Relating to the Results of the Partial International Search dated Dec. 8, 2017 in Int'l PCT Patent Appl. No. PCT/IB17/55093.
Kenny, Intra-Abdominal Pressure and Renal Function: The Venous Side of the Road, PulmCCM, Critical CareXr, GI and Nutrition, Jul. 14, 2016, accessed on line on Mar. 27, 2017 at http://pulmccm.org/main/2016/critical-care-review/intra-abdominal-pressure-renal-function/.
McCausland, et al., Dialysate Sodium, Serum Sodium and Mortality in Maintenance Hemodialysis, 27(4):1613-1618 (2012).
Medtronic Reveal LinqTM LNQ11, Insertable Cardiac Monitor, Clinician Manual, 98 pages (2015).
Munoz Mendoza, et al., Dialysate sodium and sodium gradient in maintenance hemodialysis: a neglected sodium restriction approach? Nephrol Dial Transplant, 26(4): 1281-1287 (2011).
Nakayama, et al., Clinical Effect of Low Na Concentration Dialysate (120mEq/L) for CAPD Patients, Abstracts of the XIII Annual CAPD Conference, Peritoneal Dialysis International, vol. 13, Supplement 1, 1993.
Ortiz et al., "Long-Term Automated Peritoneal Dialysis in Patients with Refractory Congestive Heart Failure," Advances in Peritoneal Dialysis, (2003), vol. 19:77-80.
Int'l Search Report dated Sep. 16, 2008 in Int'l PCT Patent Appl. No. PCT/US2005/029305.
Puttagunta, et al., Peritoneal Dialysis For Heart Failure, Peritoneal Dialysis International, 35(6):645-649 (2015.
Rosenblit et al., "Peritoneal-Urinary Drainage for Treatment of Refractory Ascites: A Pilot Study," J. of Vascular & Interventional Radiology, 9(6):998-1005 (1998).
Ruhi, et al., Use of Peritoneal Ultrafiltration in the Elderly Refractory Congestive Heart Failure Patients, Int. Urol, and Nephrol., 44(3):963-969 (2012).
Smyth, Chris, "Pump implant for cancer patients 'is a game-changer' for thousands", The Times, Health News, p. 11, Jan. 18, 2013.
www.medtronic.com/us-en/patients/treatments-therapies/fainting-heart-monitor/reveal-linq-icm.html (May 2017) (Accessed Nov. 27, 2017).
Zepeda-Orozco, et al., Dialysis Disequilibrium Syndrome, Pediatr. Nephrol, 27:2205-2211 (2012).

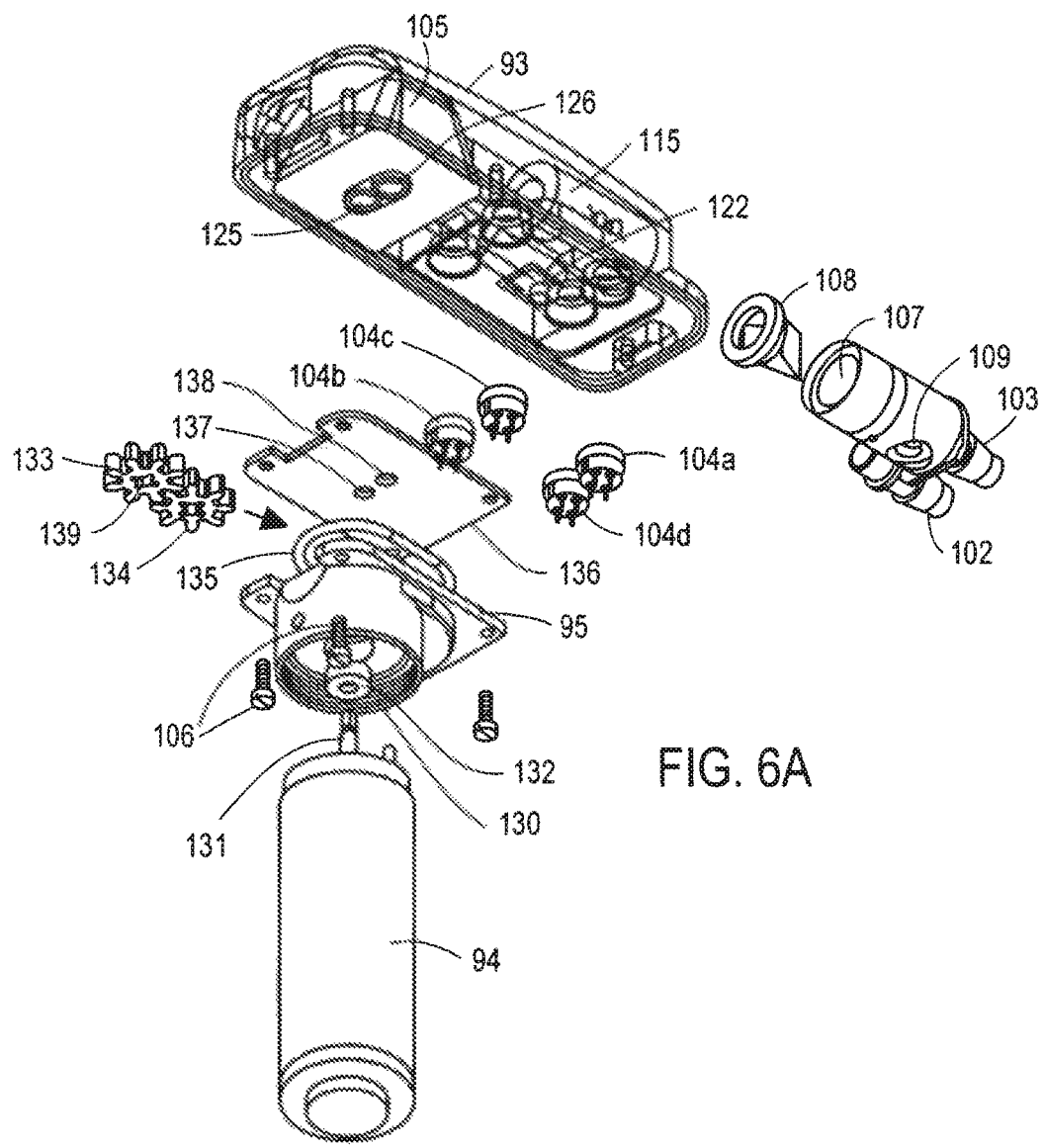
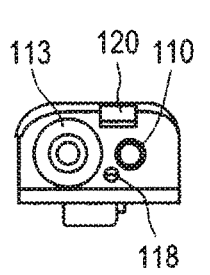
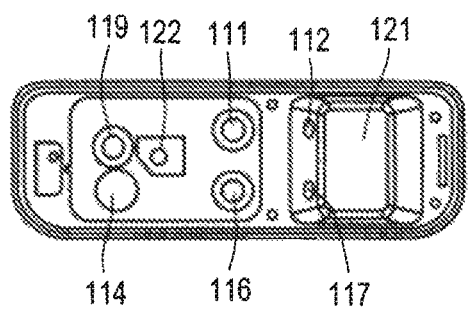
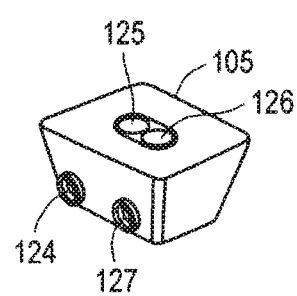
FIG. 6A
FIG. 6B
FIG. 6C
FIG. 6D

APPARATUS AND METHODS FOR TREATING INTRACORPOREAL FLUID ACCUMULATION

CROSS-REFERENCE TO RELATED APPLICATIONS

This application is a continuation under 35 U.S.C. § 120 of U.S. patent application Ser. No. 14/874,187, filed Oct. 2, 2015, now U.S. Pat. No. 10,252,037, which is a continuation of U.S. patent application Ser. No. 13/397,509, filed Feb. 15, 2012, now U.S. Pat. No. 9,149,613, which claims the benefit of U.S. Provisional Patent Application No. 61/443,668, filed Feb. 16, 2011 and entitled "Apparatus and Methods for Treating Intracorporeal Fluid Accumulation," the entire contents of each of which are incorporated herein by reference.

This application is also related to U.S. patent application Ser. No. 13/397,523, filed Feb. 15, 2012, now U.S. Pat. No. 9,039,652, the entire contents of which are incorporated herein by reference, which also claims the benefit of U.S. Provisional Patent Application No. 61/443,668, filed Feb. 16, 2011.

II. FIELD OF THE INVENTION

This application relates to apparatus and methods for treating intracorporeal fluid accumulations, such ascites, pleural effusion and pericardial effusion.

III. BACKGROUND OF THE INVENTION

There are a variety of conditions which result in pathologic chronic collection of bodily fluids within the peritoneum, pleura or pericardial sac. Chronic ascites, pleural effusion and pericardial effusion are conditions in which chronic fluid collections persist and result in increased morbidity and mortality.

These foregoing conditions currently are treated typically by one of three methods: 1) external drainage, which poses a risk of infection and long-term requirement for multiple punctures, 2) drainage to another body cavity, or 3) treatment with drugs. In pleural effusion, excess fluid arising from an underlying pathology, such as lung cancer, breast cancer or lymphoma, accumulates in the pleural cavity. If left untreated, the fluid accumulation may interfere with proper lung function, significantly increasing morbidity and mortality. Depending upon the underlying cause of the pleural effusion, treatment may consist of drug therapy, thoracentesis, in which a needle is periodically inserted through the chest and into the pleural cavity to drain the fluid accumulations, or installation of an intercostal drain, in which one end of a pigtail catheter is inserted into the pleural cavity and the fluid is drained to an external canister. Although a relatively simple procedure, placement of an intercostal drain is associated with a relatively high rate of major complications, including hemorrhage and infection. Repeated effusions also may be treated by pleurodesis, in which two pleural surfaces are attached to one another so that no fluid can accumulate between them. However, this procedure requires a lengthy hospital stay and is reported to be associated with the onset of adult respiratory distress syndrome, a potentially life-threatening complication.

In pericardial effusion, fluid accumulates in the pericardial sac and may lead to increased intrapercardial pressure and reduced cardiac output. Where the fluid accumulation interferes with proper heart function, pericardiocentesis may be performed, in which the fluid is drained to an external site through a needle or catheter inserted through the chest wall and into the pericardial sac. For chronic cases, the treatment of choice is formation of a pericardial window. In this highly invasive procedure, a section of the pericardial sac is removed to create a fistula that permits fluid to drain to the abdomen. Although this procedure is usually well tolerated by patients, the pericardial window may close, requiring re-operation.

Ascites is a highly debilitating complication associated with many medical conditions including liver failure, congestive heart failure and certain cancers. Untreated ascites can result in respiratory compromise, compression of the inferior vena cava (a vital blood vessel) and spontaneous bacterial peritonitis (a life-threatening condition). Conventional treatment for ascites includes a regime of drugs and dietary restriction, and for chronic cases, repeated surgical interventions.

The drugs often employed to treat ascites are usually long-term and often result in complications. The most common pharmaceutical treatment of ascites involves the use of diuretics to remove fluid from the patient's body through their urine. The difficulty with this treatment, however, is that fluid is removed from the entire body, including the circulating volume of blood. This in turn may result in excessive loss of fluid required to perfuse the vital organs of the human body. Thus, even with frequent application, the medicines frequently provide unsatisfactory results. In such cases, surgical, or invasive, procedures are indicated.

For chronic ascites refractory to drugs, a patient typically is required to undergo paracentesis on a regular basis, e.g., every 2-4 weeks, to drain accumulated fluid. In this procedure, peritoneal fluid is drained through the abdominal wall via the insertion of a needle through the abdominal wall into the peritoneal cavity. The regular accumulation and drainage by paracentesis of large quantities of fluid in the peritoneal cavity adversely impacts patient quality of life and often can interfere with the patient's ability to combat the underlying disease, such as cirrhosis. Moreover, repeated paracenteses place the patient at increased risk for a life-threatening infection of the peritoneal cavity. Other surgical/invasive procedures typically involve treatment of the cause of the ascites (for example, the Transjugular Intrahepatic Portosystemic Shunt) but these measures also frequently result in serious and life-threatening complications or become ineffective over time. Consequently, such procedures are performed infrequently.

Paracentesis often provides only a temporary solution in chronic cases, as the ascites quickly refills the peritoneal cavity. In particular, the presence of large quantities of fluid within the peritoneal cavity frequently disturbs the patient's fluid equilibrium, such that the patient's body attempts to compensate for fluid loss due to paracentesis by increasing ascites production. To combat this phenomenon, it is standard practice for clinicians to infuse a plasma expander, usually human albumin, into patients undergoing paracentesis. The cost of human albumin used for a typical 5-7 liter extraction can cost upwards of $500 per procedure. Consequently, regularly scheduled paracenteses followed by infusion of human albumin impose significant economic burdens on the patient and the health care system.

Previously known attempts to treat ascites have included indwelling catheters including external ports, and squeeze-bulb and magnetically-driven reciprocating pumps to transfer ascites from the peritoneal cavity into the venous vasculature, through an external port, or into the bladder. For example, U.S. Pat. No. 4,240,434 to Newkirk and U.S. Pat. No. 4,657,530 to Buchwald each describes a squeezable tube-type ascites shunt having an inlet end configured to the placed in the peritoneal cavity and an outlet end configured to be placed in a vein. Rosenblit et al., in an article entitled "Peritoneal-Urinary Drainage for Treatment of Refractory Ascites: A Pilot Study," J. Vascular & Interv. Radiology, 9(6):998-1005 (November/December 1998) describe a similar squeeze-bulb system having an outlet disposed in the bladder. U.S. Pat. No. 4,610,658 to Buchwald et al. describes an implantable pump for treating ascites that includes a magnetically-driven pump to transfer fluid from the peritoneal cavity to the vasculature system. Such previously known devices suffer from a variety of drawbacks, including fibrous encapsulation, frequent clogging and infection. Such devices provided little improvement over periodic paracenteses, and resulted in increased rates of infection, re-operation or other complications if left in place for any length of time. Moreover, a key drawback of such previously-known systems is the requirement that the patient must repeatedly locate and manually actuate the pumping mechanism on a daily basis. Such activity may be difficult for patients, especially the elderly and obese, and further complicated by an ascites-distended abdomen. Consequently, the difficulty of manipulating such previously-known systems promotes patient non-compliance, in turn leading to clogging and infection.

In view of the above-noted drawbacks of previously-known systems, it would be desirable to provide methods and apparatus for treating ascites that remove small quantities of fluid multiple times per day, and thereby avoid fluid disequilibrium caused by periodic removal of large volumes of fluid using paracentesis and concomitant use of costly plasma expanders.

It further would be particularly desirable to provide methods and apparatus for treating ascites and other intracorporeal fluid accumulations using implantable devices that are resistant to clogging, reduce risk of infection, and do not interfere with normal working of a patient's vascular system.

It also would be particularly desirable to provide methods and apparatus for treating ascites and other intracorporeal fluid accumulations using implantable devices that are configured to pump at high flow during multiple intervals daily, thereby reducing the risk of pump or catheter blockage.

It still further would be desirable to provide methods and apparatus for treating ascites and other intracorporeal fluid accumulations using implantable devices that are capable of sensing environmental conditions and that move fluid only when doing so is consistent with a patient's activity level.

IV. SUMMARY OF THE INVENTION

The present invention overcomes the drawbacks of previously-known fluid management systems for treating ascites by providing a fluid management system that automatically and autonomously removes ascites accumulations with little patient involvement. The fluid management system of the present invention preferably comprises an implantable device including a pump, a controller, a battery and a transceiver; a charging and communication system configured to periodically charge the battery of, and communicate with, the implantable device; and monitoring and control software, suitable for use with a conventional personal computer, for configuring and controlling operation of the implantable device and charging and communication system. Preferably, the monitoring and control software is available only to the treating physician, such that the patient generally interacts with the implantable device only via the charging and communication system for purposes of recharging the implantable device. In accordance with one aspect of the present invention, the implantable device is configured to pump fluid in small increments, at relatively high flow rates, during predetermined times of the day to achieve a target volume, and further is configured to periodically alter the pump position to reduce the risk of clogging of the implantable device during non-pumping intervals. The pump also may be programmed to perform a rapid sequence of backward and forward movements if a blockage is detected, thereby clearing the blockage. Additionally, the fluid management system may include one or more sensors configured to detect indicia of the onset of infection, e.g., an increase in temperature, respiratory rate, or the viscosity of ascitic fluid, and one or more alarms configured to indicate to the physician a prediction or detection of infection based on the output(s) of those sensors.

In one embodiment, the fluid management system is configured to move ascites accumulating in the peritoneal cavity to the patient's bladder in small increments on a daily basis, so that the ascitic fluid is evacuated from the body during urination. In another embodiment, designed for treating pleural effusion, the fluid management system is configured to move fluid accumulating in the pleural cavity to the patient's bladder in small increments on a daily basis, so that the effusive fluid is evacuated from the body during urination. In yet another embodiment, the implantable device is configured to have an inflow catheter that communicates with the pericardial sac to move pericardial effusion to the bladder. Alternatively, the embodiments for treating pleural and pericardial effusion may deposit the effusive fluid within the patient's peritoneal cavity (rather than the bladder), where it will be reabsorbed and excreted via the kidneys.

In one preferred embodiment, the implantable device includes an electrically-driven mechanical gear pump configured for subcutaneous implantation. The pump has an inlet port coupled to an inflow catheter and an outlet port coupled to a bladder catheter. In accordance with one aspect of the present invention, the pump employs a pair of floating gears that function as a positive displacement pump, wherein a driving gear is coupled to a splined shaft of an electric motor to minimize power consumption arising due to manufacturing variations or shaft eccentricity. The inflow catheter comprises a tube having a first end configured to be coupled to the pump inlet and a second end configured to be positioned in a selected cavity, e.g., peritoneum, pleura or pericardial sac. The second end of the inflow catheter includes a plurality of through-wall apertures that permit fluid accumulating to pass into the catheter. The bladder or outflow catheter comprises a tube having a first end configured to be coupled to the pump and a second end configured to be inserted through the wall of, and fixed within, a patient's bladder. Alternatively, for treating pleural or pericardial effusions, the second end may be configured for placement in the peritoneal cavity, rather than the bladder. The fluid circuit further includes sensors arranged to monitor ambient pressure, pressure at the pump inlet, pressure at the pump outlet, pressure in the bladder (or peritoneal cavity, if this is used as a sink), and optionally the temperature of the ascitic fluid and the respiratory rate of the patient. The inflow and outflow catheters include connectors configured to reduce the risk of improper implantation.

The implantable device further comprises a controller, packaged together with the pump, electric motor, battery, charging coil, and radio transceiver within a low volume sealed housing. The controller is coupled to the pump motor, battery, transceiver and a plurality of sensors to continually monitor pressure, temperature, humidity, charge status, pump status, patient movement and other environmental and system related parameters. The controller preferably comprises a processor, nonvolatile memory for storing firmware, implant identification information, and system and environmental data, and volatile memory that serves as a buffer for computations and instructions during execution and firmware updating. The pump motor is configured for extended use and low power consumption, and preferably includes Hall effect sensors for position sensing and to determine the direction of rotation (and correspondingly, flow and fluid viscosity). The battery preferably is a long-lasting lithium-ion or lithium polymer battery that is coupled to an inductive charging circuit, thereby enabling the battery to be recharged using the external charging and communication system. A radio frequency transceiver preferably is employed in the device for transmitting system information to, and receiving information from, the external charging and communication system, including system performance data, commands, and firmware upgrades. All of the foregoing components preferable are disposed within the housing, which further includes a filler having a low permeability for water, thereby reducing infiltration of moisture into the housing.

In accordance with one aspect of the present invention, the fluid management system includes an external charging and communication system. In a preferred embodiment, the charging and communication system comprises a housing containing a controller, radio transceiver, inductive charging circuit, power source and quality-of-charging indicator. The controller is coupled to the inductive charging circuit, power source, quality-of-charging indicator, radio transceiver, and memory for storing information to be transmitted between the monitoring and control software and implantable device. The charging and communication system preferably includes a data port, such as a USB port, or a wireless port, such as Bluetooth, Zigbee or GPRS, that permits the charging and communication system to be coupled to a conventional computer, such as a personal computer or laptop computer, configured to run the monitoring and control software. In one embodiment, the charging and communication system may include a cord that enables the system to be directly coupled to a conventional power supply, such as 120V AC wall socket. More preferably, however, the charging and communication system includes a battery-powered handpiece that periodically may be coupled to an AC powered charging base, so that the handpiece may be separated from the base to recharge the implantable device without tethering the patient with a power cord. In one preferred embodiment, the control circuitry of the charging and communication system may be configured to boost power supplied through the inductive charging circuit to the motor of the implantable device to unblock potential clogging of the gear pump.

The fluid management system further comprises monitoring and control software that preferably is accessible only to the patient's physician. The software is configured to run on a conventional personal computer or laptop computer, and enables the physician to configure and monitor operation of the charging and communication system and implantable device. The software may include routines for controlling any of a number of parameters associated with the pump operation, such as a target amount of fluid to move daily or per motor actuation, and limits for inflow catheter pressure, bladder pressure, pump pressure, and implant temperature. The software also may be configured to control operation of the implantable device so as not to move fluid during specific periods (e.g., at night) or to defer pump actuation if the patient is asleep. The software further may be configured, for example, to send immediate commands to the implantable device to start or stop the pump, or to operate the pump in reverse or at high power to unblock the pump or its associated catheters, such as when the patient is visiting his or her physician. The software may be configured to download data collected from the implantable device and stored on the charging and communication system, such as during a patient visit to the physician's office. Optionally, based on the downloaded information, such as the patient's respiratory rate, temperature, and fluid viscosity, the software may be configured to alert the physician of a prediction or detection of infection.

It is contemplated that the system of the present invention may avoid difficulties typically associated with the previously-known apparatus and methods for addressing ascites. It is expected, for instance, that the system and methods of the present invention will enable small quantities of peritoneal fluid to be moved to the bladder without the inconvenience and complications generally associated with use of pharmaceuticals or paracenteses. In particular, because the apparatus and methods of the present invention avoid repeated, periodic removal of large quantities of fluid, as occurs with paracenteses, the tendency to generate additional ascites to offset the removed fluid will be reduced. These effects in turn are expected to obviate the need to infuse plasma expanders, such as human albumin, into the patient following paracentesis, thereby resulting in significant cost savings to the patient and health care system. The prediction or detection of infection, particularly at an early stage of infection, further may improve patient outcomes and reduce the need for more expensive treatments. Finally, the apparatus and methods of the present invention are expected to provide improved quality of life for chronic ascites patients, allowing such patients to pursue less sedentary lifestyles than would otherwise be possible, and encouraging better compliance with medically-directed dietary and exercise regimes.

In an alternative embodiment, a fluid management system is provided generally as described above, but instead configured for treating pleural or pericardial effusion. As discussed above, few surgical options are available for treating these conditions, and most of those present significant risks for morbidity and morality. In particular, the system of the present invention may be configured for treating pleural or pericardial effusion, and comprises an implantable device, a charging and communication system and software substantially as described above. This embodiment differs from the ascites fluid management system of the present invention primarily in that the pump has an inflow catheter coupled to a pleural or pericardial cavity, the controller is configured to work under negative pressures, and the outflow catheter may deposit the drained fluid into the peritoneal cavity. More particularly, the inflow catheter has a first end configured to be coupled to the pump inlet and a second end configured to be positioned in the pleural or pericardial cavity, and includes a plurality of through-wall apertures that permit fluid accumulating in the cavity to pass into the catheter without interfering with proper functioning of the lungs or heart. As some fluid is required to lubricate movement of the organ within these cavities, the implantable device preferably is programmed not to pump all of the fluid from the cavity. In addition, the implantable device is programmed to interpret and provide drainage that accounts for pressure fluctuations arising in the cavity during normal respiration or cardiac activity.

Methods of implanting and operating the fluid management system of the present invention also are provided. The implantable device preferably may be placed subcutaneously using interventional radiologic techniques including radiographic imaging or ultrasound, while the inflow catheter and outflow catheter may be placed using surgical, or more preferably, minimally invasive procedures. The inflow catheter, in one variation, may be tunneled subcutaneously to the site of drainage and the outflow tubing can be subcutaneously channeled to the bladder (or peritoneal cavity). The implantable device preferably is programmed using radio frequency coupling of the transceivers in the implantable device and charging and communication system, while power is supplied to the battery of the implantable device by coupling the inductive charging circuits of the implantable device and charging and communication system. Additional details of methods of implanting and operating a system in accordance with the present invention are described below.

V. BRIEF DESCRIPTION OF THE DRAWINGS

FIGS. 6A, 6B, 6C and 6D are, respectively, an exploded perspective view of the drive assembly of the implantable device; front and plan views of the upper housing; and a perspective view of the manifold of an exemplary embodiment of the implantable device.

VI. DETAILED DESCRIPTION OF THE INVENTION

The fluid management system of the present invention comprises devices for facilitating removal of fluid from a body region, such as the peritoneum, pleural cavity or pericardial sac, where drainage is desired. The devices disclosed herein may be utilized for drainage of chronic excess fluid accumulation from one body cavity to a second body cavity, preferably the urinary bladder. In accordance with the principles of the present invention, the fluid management system may be optimized for use in treating chronic ascites, and pleural or pericardial effusion, and optionally may be configured to alert the physician as to a prediction or detection of infection.

System Overview

Figure 1:
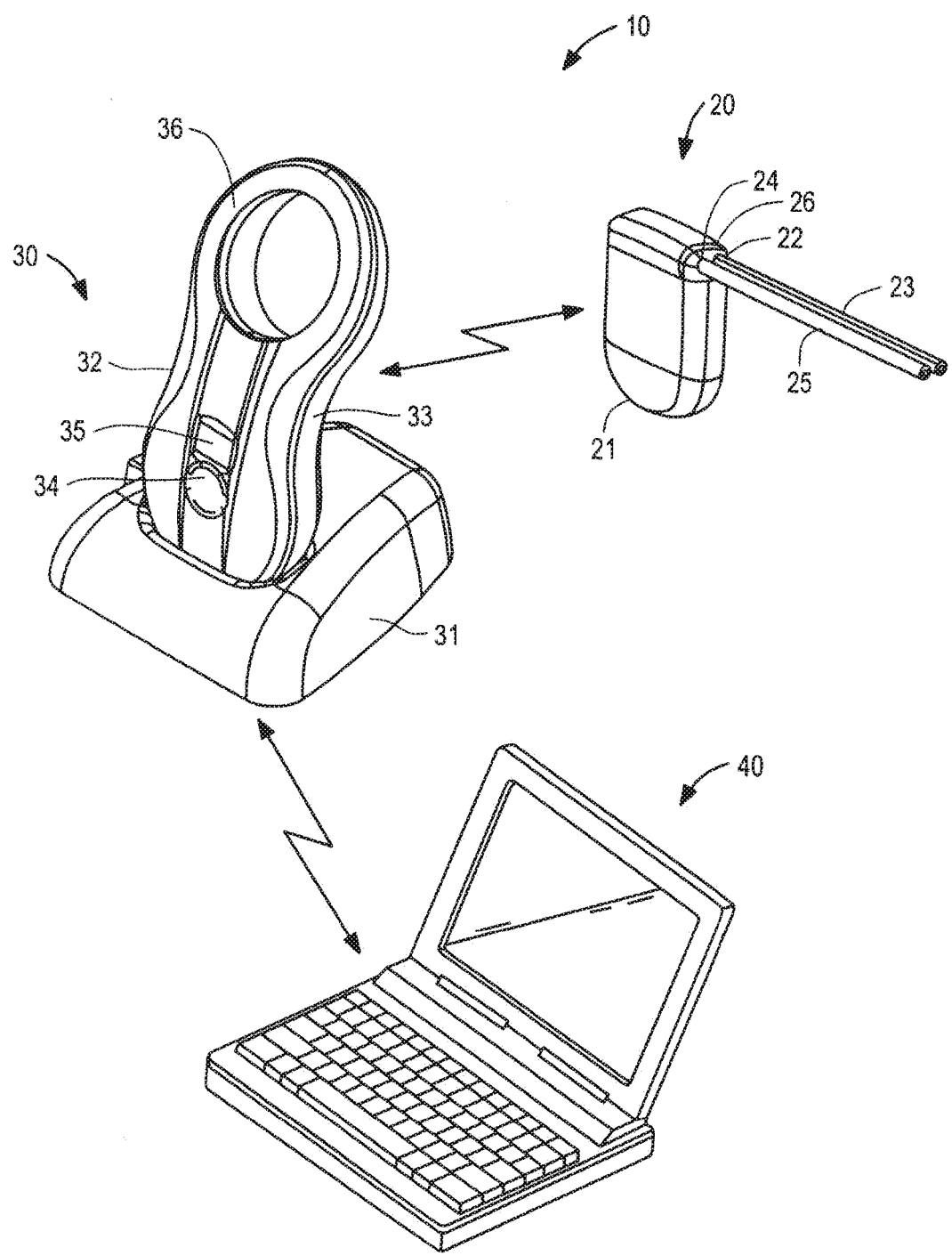
FIG. 1 is a perspective view of the components of an exemplary fluid management system constructed in accordance with the principles of the present invention.

Referring to FIG. 1, an overview of fluid management system 10 of the present invention is provided. In FIG. 1, components of the system are not depicted to scale on either a relative or absolute basis. Fluid management system 10 comprises implantable device 20, external charging and communication system 30, and a software-based monitoring and control system 40. In the illustrated embodiment, monitoring and control system 40 is installed and run on a conventional laptop computer used by the patient's physician. During patient visits, charging and communication system 30 may be coupled, either wirelessly or using a cable, to monitoring and control system 40 to download for review data stored on implantable device 20, or to adjust the operational parameters of the implantable device. Monitoring and control system 40 also may be configured to upload and store date retrieved from charging and communication system 30 to a remote server for later access by the physician or charging and communications system 30.

Implantable device 20 comprises an electromechanical pump having housing 21 configured for subcutaneous implantation. As described in further detail below, in an embodiment suitable for treating ascites, implantable device 20 includes an electrically-driven mechanical gear pump having inlet port 22 coupled to peritoneal catheter 23 and outlet port 24 coupled to bladder catheter 25. Peritoneal catheter 23 comprises a tube having a first end configured to be coupled to pump inlet 23 and a second end configured to be positioned in the peritoneal cavity. Bladder catheter 25 comprises a tube having a first end configured to be coupled to pump outlet 24 and a second end configured to be inserted through the wall of, and fixed within, a patient's bladder. In a preferred embodiment, both catheters are made of medical-grade silicone and include polyester cuffs at their distal ends (not shown) to maintain the catheters in position. Peritoneal catheter 23 and bladder catheter 25 are coupled to pump housing 21 using connector 26 configured to reduce the risk of improper installation and inadvertent disconnection, and may in addition include distinct cross-sections that reduce the risk of improper installation.

Implantable device 20 preferably is configured to move fluid in short (e.g., 10 second) intervals (e.g., every 10-20 minutes). Such short but frequent intervals are expected to overcome the clogging issues common to previously-known ascites shunts, by preventing the accumulation of material on the interior lumens of catheters 23 and 25, and reducing the risk for tissue ingrowth. For ascites treatment, the fluid circuit of implantable device 20 preferably is configured to provide an average flow rate of about 60 ml/hour, although much higher and lower flow rates are possible if needed. As described in detail below, the pumping time and volume, including maximum and minimum limits for daily pumped volume, may be programmed by the physician using monitoring and control system 40 as required for a specific patient. As further described below, the fluid circuit of implantable device 20 includes pressure sensors that monitor pressure in both the peritoneal cavity and the bladder, such that pumping of fluid into the bladder is disabled until the bladder is determined to have sufficient space to accommodate additional fluid. For patient comfort, implantable device 10 normally is programmed not to pump at night or when an accelerometer included in the implantable device indicates that the patient is asleep (and thus unlikely to be able to void the bladder). Implantable device 20 preferably includes multiple separate fail-safe mechanisms, to ensure that urine cannot pass from the bladder to the peritoneal cavity through the pump, thereby reducing the risk of transmitting infection.

Still referring to FIG. 1, external charging and communication system 30 in a preferred form comprises base 31 and handpiece 32. In this embodiment, handpiece 32 contains a controller, a radio transceiver, an inductive charging circuit, a battery, a quality-of-charging indicator and a display, and is removably coupled to base 31 to recharge its battery. Base 31 may contain a transformer and circuitry for converting conventional 120V power service to a suitable DC current to charge handpiece 32 when coupled to base 31. In alternative embodiments, handpiece 32 may include such circuitry and a detachable power cord, thereby permitting the handpiece to be directly plugged into a convention 120V wall socket to charge the battery. In a preferred embodiment, each of implantable device 20 and handpiece 32 includes a device identifier stored in memory, such that handpiece 32 provided to the patient is coded to operate only with that patient's specific implantable device 20.

Handpiece 32 preferably includes housing 33 having multi-function button 34, display 35, a plurality of light emitting diodes (LEDs, not shown) and inductive coil portion 36. Multi-function button 34 provides the patient the ability to issue a limited number of commands to implantable device 20, while display 35 provides visible confirmation that a desired command has been input; it also displays battery status. Inductive coil portion 36 houses an inductive coil that is used transfer energy from handpiece 32 to recharge the battery of implantable device 20. The LEDs, which are visible through the material of housing 33 when lit, may be arranged in three rows of two LEDs each, and are coupled to the control circuitry and inductive charging circuit contained within handpiece 32. As described in further detail below, the LEDs may be arranged to light up to reflect the degree of inductive coupling achieved between handpiece 32 and implantable device 20 during recharging of the latter. Alternatively, the LEDs may be omitted and an analog display provided on display 35 indicating the quality of inductive coupling.

As further described in detail below, the control circuitry contained within handpiece 32 is coupled to the inductive charging circuit, battery, LEDs and radio transceiver, and includes memory for storing information from implantable device 20. Handpiece 32 also preferably includes a data port, such as a USB port, that permits the handpiece to be coupled to monitoring and control system 40 during visits by the patient to the physician's office. Alternatively, handpiece 32 may include a wireless chip, e.g., conforming to the Bluetooth or IEEE 802.11 wireless standards, thereby enabling the handpiece to communicate wirelessly with monitoring and control system 40.

Monitoring and control system 40 is intended primarily for use by the physician and comprises software configured to run on a conventional laptop computer. The software enables the physician to configure, monitor and control operation of charging and communication system 30 and implantable device 20. As described in detail below, the software may include routines for configuring and controlling pump operation, such as a target amount of fluid to move daily or per motor actuation, intervals between pump actuation, and limits on peritoneal cavity pressure, bladder pressure, pump pressure, and battery temperature. System 40 also may provide instructions to implantable device 20 via charging and control system 30 to control operation of implantable device 20 so as not to move fluid during specific periods (e.g., at night) or to defer pump actuation if the patient is asleep. System 40 further may be configured, for example, to send immediate commands to the implantable device to start or stop the pump, or to operate the pump in reverse or at high power to unblock the pump or associated catheters. The software of system 40 also may be configured to download real-time data relating to pump operation, as well as event logs stored during operation of implantable device 20. Based on the downloaded data, e.g., based on measurements made of the patient's temperature, respiratory rate, and/or fluid viscosity, the software of system 40 optionally may be configured to alert the physician to a prediction or detection of infection. Finally, system 40 optionally may be configured to remotely receive raw or filtered operational data from a patient's handpiece 32 over a secure Internet channel.

Inflow and Outflow Catheters

Figure 2A:
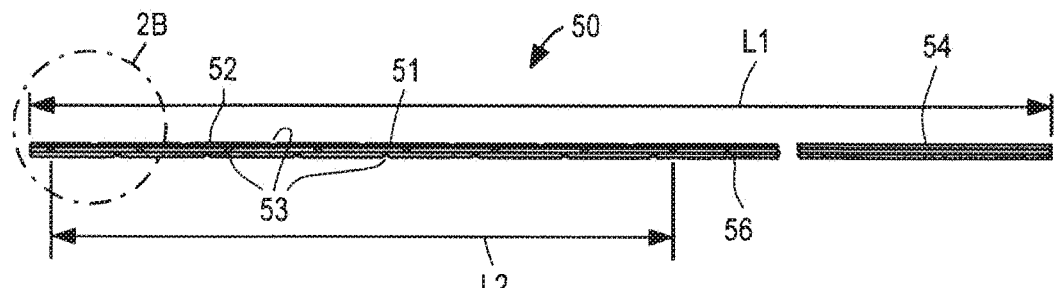
FIGS. 2A and 2B are, respectively, side view and perspective detailed views of an exemplary embodiment of an inflow catheter suitable for use with the system of the present invention, in which FIG. 2B corresponds to detail region 2B of FIG. 2A.
Figure 2B:
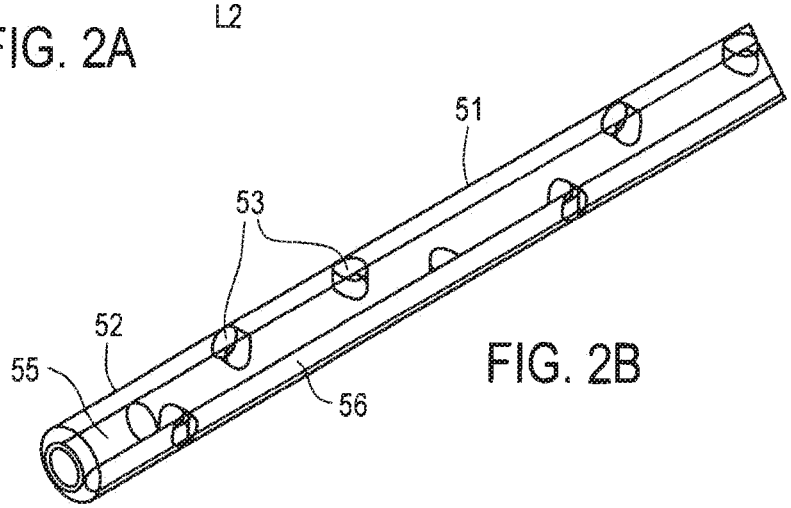

Referring to FIGS. 2A and 2B, exemplary inflow catheter 50 constructed in accordance with the principles of the present invention is described. Inflow catheter 50 may be configured for use in the peritoneal cavity (and thus correspond to peritoneal catheter 23 of FIG. 1) or pleural or pericardial cavity, and preferably comprises tube 51 of medical-grade silicone including inlet end 52 having a plurality of through-wall holes 53 and outlet end 54. When configured for placement in the peritoneal cavity, inflow catheter preferably has length L1 of about 40 cm, with holes 53 extending over length L2 of about 24 cm from inlet end 52. Holes 53 preferably are arranged circumferentially offset by about 90° and longitudinally offset between about 8 mm to 10 mm, as shown in FIG. 2B. In one preferred embodiment, 29 holes 53 are arranged in four rows of 7 holes each, extend only through one wall of the inflow catheter at each location, and have a size of between 2.0 to 2.5 mm. Inflow catheter 50 preferably includes solid silicone plug 55 that fills distal end of the lumen for a distance of about 7-10 mm to reduce tissue ingrowth, and radiopaque strip 56 disposed on, or embedded within, the catheter that extends the entire length of the catheter, that renders the catheter visible in fluoroscopic or X-ray images. Inflow catheter 50 may also include a polyester cuff in the region away from holes 53, to promote adhesion of the catheter to the surrounding tissue, thereby anchoring it in place.

Alternatively, inlet end 52 of inflow catheter 50 may have a spiral configuration, and an atraumatic tip, with holes 53 distributed over a length of the tubing to reduce the risk of clogging. As a further alternative, inlet end 52 may include a portion having an enlarged diameter, as disclosed in U.S. Pat. No. 4,657,530, or a reservoir as disclosed in FIGS. 9 to 16 of U.S. Patent Application Publication US 2009/0318844, the entire contents of both of which are incorporated herein by reference, to further reduce the risk of clogging. Inlet end 52 also may terminate in a duck-bill valve, as shown for example in U.S. Pat. No. 4,240,434, thereby permitting the catheter to be cleaned in situ by disconnecting the outlet end of the catheter from implantable device 20 and extending a rod from the outlet end of catheter 50 through the duckbill valve at the inlet end.

Inlet end 52 also may include a polyester cuff to promote adhesion of the catheter to an adjacent tissue wall, thereby ensuring that the inlet end of the catheter remains in position. Outlet end 54 also may include a connector for securing the outlet end of the inflow catheter to implantable device 20. In one preferred embodiment, the distal end of the inflow catheter, up to the ingrowth cuff, may be configured to pass through a conventional 16 F peel-away sheath. In addition, the length of the inflow catheter may be selected to ensure that it lays along the bottom of the body cavity, and is sufficiently resistant to torsional motion so as not to become twisted or kinked during or after implantation.

Figure 3A:
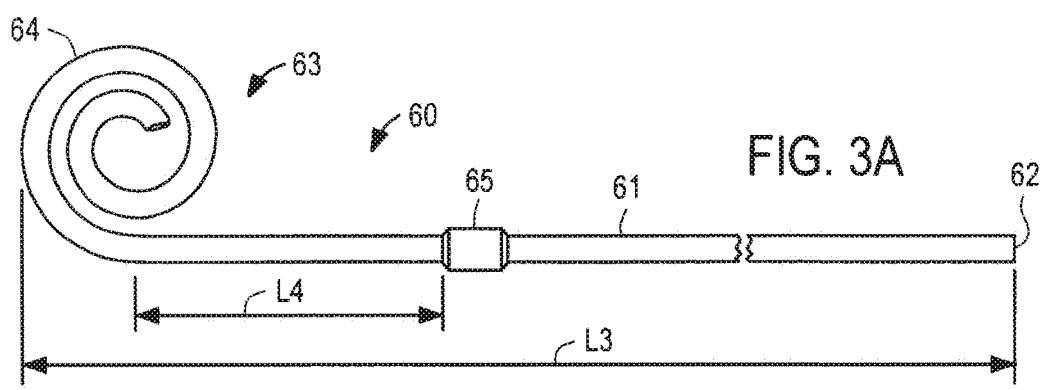
FIGS. 3A and 3B are, respectively, side and perspective views, respectively, of first and second embodiments of bladder catheters suitable for use with the ascites treatment system of the present invention.

With respect to FIG. 3A, a first embodiment of outflow catheter 60 of the present invention is described, corresponding to bladder catheter 25 of FIG. 1. Outflow catheter 60 preferably comprises tube 61 of medical-grade silicone having inlet end 62 and outlet end 63 including spiral structure 64, and polyester ingrowth cuff 65. Outflow catheter 60 includes a single internal lumen that extends from inlet end 62 to a single outlet at the tip of spiral structure 64, commonly referred to as a "pigtail" design. Inlet end 62 may include a connector for securing the inlet end of the outflow catheter to implantable device 20, or may have a length that can be trimmed to fit a particular patient.

When configured for use as the outflow catheter in an ascites treatment system, outflow catheter may have length L3 of about 45 cm, with cuff 65 placed length L4 of about 5 to 6 cm from spiral structure 64. Outflow catheter 60 may be loaded onto a stylet with spiral structure 64 straightened, and implanted using a minimally invasive technique in which outlet end 63 and spiral structure 64 are passed through the wall of a patient's bladder using the stylet. When the stylet is removed, spiral structure 64 returns to the coiled shape shown in FIG. 3A. Once outlet end 63 of outflow catheter 60 is disposed within the patient's bladder, the remainder of the catheter is implanted using a tunneling technique, such that inlet end 62 of the catheter may be coupled to implantable device 20. Spiral structure 64 may reduce the risk that outlet end 63 accidentally will be pulled out of the bladder before the tissue surrounding the bladder heals sufficiently to incorporate ingrowth cuff 65, thereby anchoring the outflow catheter in place.

In a preferred embodiment, the outflow catheter is configured to pass through a conventional peel-away sheath. Outflow catheter 60 preferably is sufficiently resistant to torsional motion so as not to become twisted or kinked during or after implantation. In a preferred embodiment, inflow catheter 50 and outflow catheter 60 preferably are different colors, have different exterior shapes (e.g., square and round) or have different connection characteristics so that they cannot be inadvertently interchanged during connection to implantable device 20. Optionally, outflow catheter 60 may include an internal duckbill valve positioned midway between inlet 62 and outlet end 63 of the catheter to insure that urine does not flow from the bladder into the peritoneal cavity if the outflow catheter is accidentally pulled free from the pump outlet of implantable device 20.

In an alternative embodiment, the inflow and outflow catheters devices may incorporate one or several anti-infective agents to inhibit the spread of infection between body cavities. Examples of anti-infective agents which may be utilized may include, e.g., bacteriostatic materials, bacteriocidal materials, one or more antibiotic dispensers, antibiotic eluting materials, and coatings that prevent bacterial adhesion, and combinations thereof.

Alternatively, rather than comprising separate catheters, inflow and outflow catheters may share a common wall. This arrangement may be utilized ideally for an ascites treatment embodiment because the bladder and peritoneal cavity share a common wall, thereby facilitating insertion of a single dual-lumen tube. In addition, either or both of the inflow or outflow catheters may be reinforced along a portion of its length or along its entire length using ribbon or wire braiding or lengths of wire or ribbon embedded or integrated within or along the catheters. The braiding or wire may be fabricated from metals such as stainless steels, superelastic metals such as nitinol, or from a variety of suitable polymers.

Figure 3B:
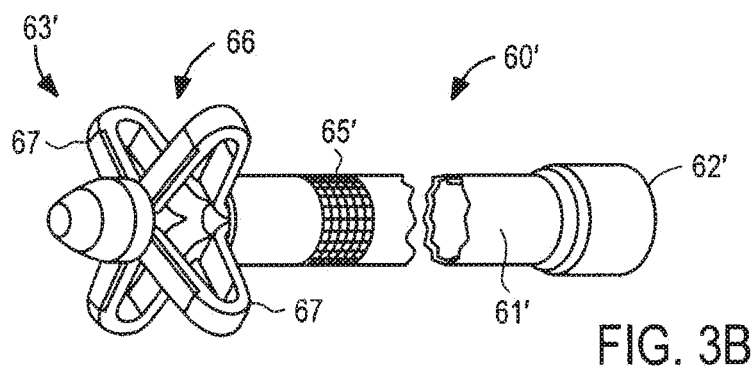

With respect to FIG. 3B, a second embodiment of an outflow catheter of the present invention is described, in which similar components are identified with like-primed numbers. Outflow catheter 60' preferably comprises tube 61' of medical-grade silicone having inlet end 62', outlet end 63' and polyester ingrowth cuff 65'. In accordance with this embodiment, outlet end 63' includes malecot structure 66, illustratively comprising four resilient wings 67 that expand laterally away from the axis of the catheter to reduce the risk that outlet end 63' of the catheter will be inadvertently pulled loose after placement. Inlet end 62' may include a connector for securing the inlet end of the outflow catheter to implantable device 20, or may have a length that can be trimmed to fit a particular patient.

Malecot structure 66 preferably is constructed so that wings 67 deform to a substantially flattened configuration when a stylet is inserted through the lumen of the catheter. In this manner, outflow catheter 60' may be loaded onto a stylet, and using a minimally invasive technique, outlet end 63' and malecot structure 66 may be passed through the wall of a patient's bladder using the stylet. When the stylet is removed, wings 67 of the malecot structure return to the expanded shape shown in FIG. 3B. Once outlet end 63' of outflow catheter 60' is coupled to the patient's bladder, the remainder of the catheter is implanted using a tunneling technique, such that inlet end 62' of the catheter may be coupled to implantable device 20. Malecot structure 66 may reduce the risk that outlet end 63' accidentally will be pulled out of the bladder before the tissue surrounding the bladder heals sufficiently to incorporate ingrowth cuff 65'. As for the embodiment of FIG. 3A, the outflow catheter of FIG. 3B may be configured to pass through a conventional peel-away sheath, and preferably is sufficiently resistant to torsional motion so as not to become twisted or kinked during or after implantation.

As mentioned above, for ascites treatment systems, the outlet end of the outflow catheter preferably is configured for placement in the urinary bladder, and this configuration also may be employed for pleural effusion and pericardial effusion treatment systems. Alternatively, the outflow catheter used for systems designed for treatment of pleural or pericardial effusions may be configured so that the outlet end is disposed in the peritoneal cavity, such that effusive fluid drained into the peritoneal cavity is reabsorbed and excreted, e.g., through the kidneys. For such embodiments, outflow catheter 60 may be constructed similar to inflow catheter 50 of FIG. 2, and may have a plurality of holes to drain fluid into the peritoneal cavity.

The Implantable Device

Figure 4:
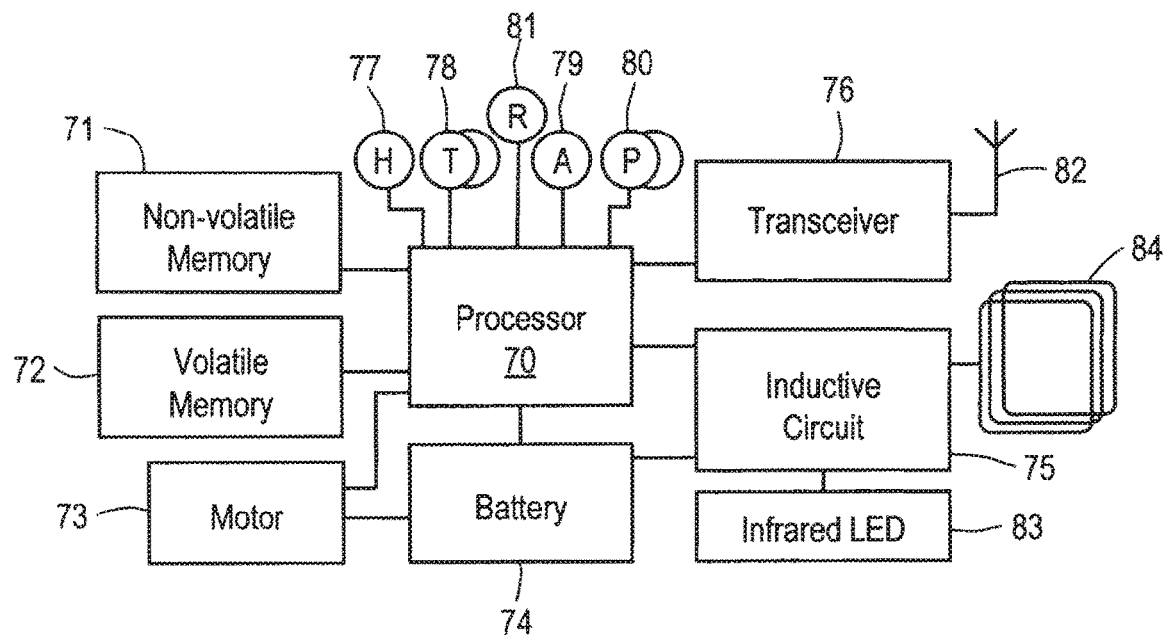
FIG. 4 is a schematic diagram of the electronic components of an exemplary embodiment of the implantable device of the present invention.
Figures 5A, 5B:
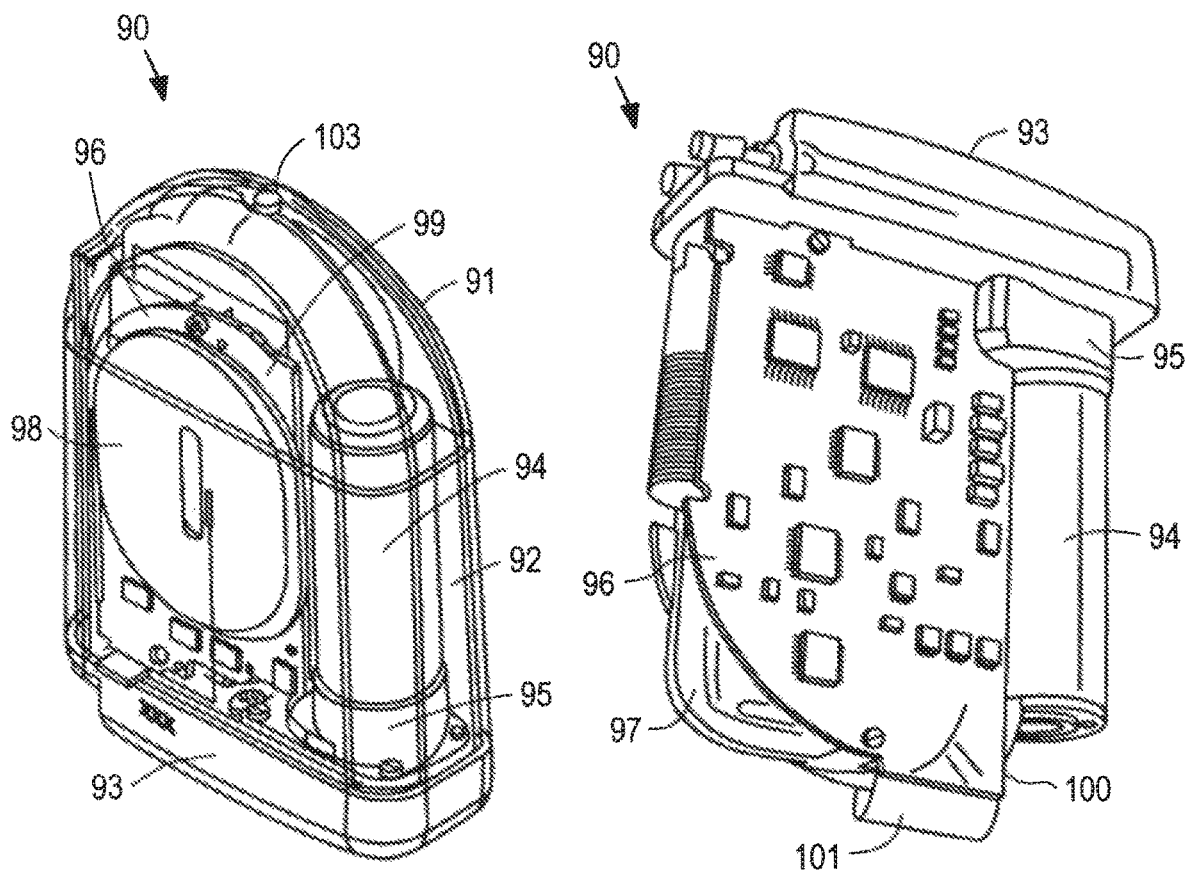
FIGS. 5A and 5B are, respectively, a perspective view of the implantable device of the present invention with the housing shown in outline and a perspective view of the obverse side of the implantable device with the housing and low water permeable filler removed.

Referring now to FIG. 4, a schematic depicting the functional blocks of implantable device 20 of the present invention is described. Implantable device 20 includes control circuitry, illustratively processor 70 coupled to nonvolatile memory 71, such as flash memory or electrically erasable programmable read only memory, and volatile memory 72 via data buses. Processor 70 is electrically coupled to electric motor 73, battery 74, inductive circuit 75, radio transceiver 76 and a plurality of sensors, including humidity sensor 77, a plurality of temperature sensors 78, accelerometer 79, a plurality of pressure sensors 80, and respiratory rate sensor 81. Inductive circuit 75 is electrically coupled to coil 84 to receive energy transmitted from charging and communication system 30, while transceiver 76 is coupled to antenna 82, and likewise is configured to communicate with a transceiver in charging and communication system 30, as described below. Optionally, inductive circuit 75 also may be coupled to infrared light emitting diode 83. Motor 73 may include a dedicated controller, which interprets and actuates motor 73 responsive to commands from processor 70. All of the components depicted in FIG. 4 are contained within a low volume sealed biocompatible housing, as shown in FIG. 5A.

Processor 70 executes firmware stored in nonvolatile memory 71 which controls operation of motor 73 responsive to signals generated by motor 73, sensors 77-81 and commands received from transceiver 76. Processor 70 also controls reception and transmission of messages via transceiver 76 and operation of inductive circuit 75 to charge battery 74. In addition, processor 70 receives signals generated by Hall Effect sensors located within motor 73, which are used to compute direction and revolutions of the gears of the gear pump, and thus fluid volume pumped and the viscosity of that fluid, as described below. Processor 70 preferably includes a low-power mode of operation and includes an internal clock, such that the processor can be periodically awakened to handle pumping, pump tick mode, or communications and charging functions, and/or awakened to handle commands received by transceiver 76 from handpiece 32. In one embodiment, processor 70 comprises a member of the MSP430 family of microcontroller units available from Texas Instruments, Incorporated, Dallas, Tex., and may incorporate the nonvolatile memory, volatile memory, and radio transceiver components depicted in FIG. 4. In addition, the firmware executed on processor 70 may be configured to respond directly to commands sent to implantable device 20 via charging and communication system 30. Processor 70 also is configured to monitor operation of motor 72 (and any associated motor controller) and sensors 78-81, as described below, and to store data reflecting operation of the implantable device, including event logs and alarms. Thus, data is reported to the charging and communication system when it is next wirelessly coupled to the implantable device. In a preferred embodiment, processor 70 generates up to eighty log entries per second prior to activating the pump, about eight log entries per second when the implantable system is actively pumping and about one log entry per hour when not pumping.

Nonvolatile memory 71 preferably comprises flash memory or EEPROM, and stores a unique device identifier for implantable device 20, firmware to be executed on processor 70, configuration set point data relating to operation of the implantable device, and optionally, coding to be executed on transceiver 76 and/or inductive circuit 75, and a separate motor controller, if present. Firmware and set point data stored on nonvolatile memory 71 may be updated using new instructions provided by control and monitoring system 40 via charging and communication system 30. Volatile memory 72 is coupled to and supports operation of processor 70, and stores data and event log information gathered during operation of implantable device 20. Volatile memory 72 also serves as a buffer for communications sent to, and received from, charging and communication system 30.

Transceiver 76 preferably comprises a radio frequency transceiver and is configured for bi-directional communications via antenna 76 with a similar transceiver circuit disposed in handpiece 32 of charging and communication system 30. Transceiver 76 also may include a low power mode of operation, such that it periodically awakens to listen for incoming messages and responds only to those messages including the unique device identifier assigned to that implantable device. Alternatively, because transceiver 76 communicates only with the corresponding transceiver in handpiece 32 of its associated charging and communication system 30, transceiver 76 may be configured to send or receive data only when inductive circuit 75 of the implantable device is active. In addition, transceiver 76 may employ an encryption routine to ensure that messages sent from, or received by, the implantable device cannot be intercepted or forged.

Inductive circuit 75 is coupled to coil 84, and is configured to recharge battery 74 of the implantable device when exposed to a magnetic field supplied by a corresponding inductive circuit within handpiece 32 of charging and communication system 30. In one embodiment, inductive circuit 75 is coupled to optional infrared LED 83 that emits an infrared signal when inductive circuit 75 is active. The infrared signal may be received by handpiece 32 of charging and communication system 30 to assist in locating the handpiece relative to the implantable device, thereby improving the magnetic coupling and energy transmission to the implantable device.

In accordance with one aspect of the present invention, inductive circuit 75 optionally may be configured not only to recharge battery 74, but to directly provide energy to motor 73 in a "boost" mode or jog/shake mode to unblock the pump. In particular, if processor 70 detects that motor 73 is stalled, e.g., due to a block created by the proteinaceous ascitic fluid, an alarm may be stored in memory. When implantable device 20 next communicates with charging and communication system 30, the alarm is reported to handpiece 32, and the patient may be given the option of depressing multifunction button 34 to apply an overvoltage to motor 73 from inductive circuit 75 for a predetermined time period to free the pump blockage. Alternatively, depressing the multi-function button may cause processor 70 to execute a set of commands by which motor 73 is jogged or shaken, e.g., by alternatingly running the motor is reverse and then forward, to disrupt the blockage. Because such modes of operation may employ higher energy consumption than expected during normal operation, it is advantageous to drive the motor during such procedures with energy supplied via inductive circuit 75.

Battery 74 preferably comprises a lithium ion or lithium polymer battery capable of long lasting operation, e.g., up to three years, when implanted in a human, so as to minimize the need for re-operations to replace implantable device 20. In one preferred embodiment, battery 74 supplies a nominal voltage of 3.6V, a capacity of 150 mAh when new, and a capacity of about 120 mAh after two years of use. Preferably, battery 74 is configured to supply a current of 280 mA to motor 73 when pumping; 25 mA when the transceiver is communicating with charging and communication system 30; 8 mA when processor 70 and related circuitry is active, but not pumping or communicating; and 0.3 mA when the implantable device is in low power mode. More preferably, battery 74 should be sized to permit a minimum current of at least 450 mAh for a period of 10 seconds and 1 A for 25 milliseconds during each charging cycle.

Motor 73 preferably is a brushless direct current or electronically commuted motor having a splined output shaft that drives a set of floating gears that operate as a gear pump, as described below. Motor 73 may include a dedicated motor controller, separate from processor 70, for controlling operation of the motor. Motor 73 may include a plurality of Hall Effect sensors, preferably two or more, for determining motor position and direction of rotation. Due to the high humidity that may be encountered in implantable device 20, processor 70 may include programming to operate motor 73, although with reduced accuracy, even if some or all of the Hall Effect sensors fail.

In a preferred embodiment, motor 73 is capable of driving the gear pump to generate a nominal flow rate of 150 ml/min and applying a torque of about 1 mNm against a pressure head of 30 cm water at 3000 RPM. In this embodiment, the motor preferably is selected to drive the gears at from 1000 to 5000 RPM, corresponding to flow rates of from 50 to 260 ml/min, respectively. The motor preferably has a stall torque of at least 3 mNm at 500 mA at 3 V, and more preferably 6 mNm in order to crush non-solid ascitic proteinaceous materials. As discussed above, the motor preferably also supports a boost mode of operation, e.g., at 5 V, when powered directly through inductive circuit 75. Motor 73 preferably also is capable of being driven in reverse as part of a jogging or shaking procedure to unblock the gear pump.

In accordance with one aspect of the present invention, processor 70 may be programmed to automatically and periodically wake up and enter a pump tick mode. In this mode of operation, the gear pump is advanced slightly, e.g., about 120° as measured by the Hall Effect sensors, before processor 70 returns to low power mode. Preferably, this interval is about every 20 minutes, although it may be adjusted by the physician using the monitoring and control system. This pump tick mode is expected to prevent the ascitic fluid, which has a high protein content, from partially solidifying, and blocking the gear pump, and is expected to be especially advantageous in overcoming the problem of clogging observed in previously-known implantable systems designed to treat chronic ascites.

In addition, processor 70 also may be programmed to enter a jog or shake mode when operating on battery power alone, to unblock the gear pump. Similar to the boost mode available when charging the implantable device with the handpiece of charging and communication system 30, the jog or shake mode causes the motor to rapidly alternate the gears between forward and reverse directions to crush or loosen and proteinaceous buildup in the gear pump or elsewhere in the fluid path. Specifically, in this mode of operation, if the motor does not start to turn within a certain time period after it is energized (e.g. 1 second), the direction of the motion is reversed for a short period of time and then reversed again to let the motor turn in the desired direction. If the motor does still not turn (e.g., because the gear pump is jammed) the direction is again reversed for a period of time (e.g., another 10 msec). If the motor still is not able to advance the time interval between reversals of the motor direction is reduced to allow for the motor to develop more power, resulting in a shaking motion of the gears. If the motor does not turn forward for more than 4 seconds, the jog mode of operation is stopped, and an alarm is written to the event log. If the motor was unable to turn forward, processor 70 will introduce a backwards tick before the next scheduled fluid movement. A backward tick is the same as a tick (e.g., about 120° forward movement of the motor shaft) but in the reverse direction, and is intended to force the motor backwards before turning forward, which should allow the motor to gain momentum.

Sensors 77-81 continually monitor humidity, temperature, acceleration, pressure, and respiratory rate, and provide corresponding signals to processor 70. In particular, humidity sensor 77 is arranged to measure humidity within the housing of the implantable device, to ensure that the components of implantable device are operated within expected operational limits. Humidity sensor 77 preferably is capable of sensing and reporting humidity within a range or 20% to 100% with high accuracy. One or more of temperature sensors 78 may be disposed within the housing and monitor the temperature of the implantable device, and in particular battery 74 to ensure that the battery does not overheat during charging, while another one or more of temperature sensors 78 may be disposed so as to contact fluid entering at inlet 62 and thus monitor the temperature of the fluid, e.g., for use in predicting or detecting infection on the basis of an increase in the fluid's temperature. Accelerometer 79 is arranged to measure acceleration of the implant, preferably along at least two axes, to detect periods of inactivity, e.g., to determine whether the patient is sleeping. This information is provided to processor 70 to ensure that the pump is not operated when the patient is indisposed to attend to voiding of the bladder.

Implantable device 20 preferably includes multiple pressure sensors 80, which are continually monitored during waking periods of the processor. As described below with respect to FIG. 6A, the implantable device of the present invention preferably includes four pressure sensors: a sensor to measure the pressure in the source cavity (e.g., peritoneal, pleural or pericardial cavity), a sensor to measure the ambient pressure, a sensor to measure the pressure at the outlet of the gear pump, and a sensor to measure the pressure in the sink cavity (e.g., bladder, or for pleural or pericardial systems, the peritoneal cavity). These sensors preferably are configured to measure absolute pressure between 450 mBar and 1300 mBar while consuming less than 50 mW at 3V. Preferably, the sensors that measure pressure at the pump outlet and in the sink are placed across a duckbill valve, which prevents reverse flow into the gear pump and also permits computation of flow rate based on the pressure drop across the duckbill valve.

Respiratory rate monitor 81 is configured to measure the patient's respiratory rate, e.g., for use in predicting or detecting infection based on an increase in the patient's respiratory rate. Alternatively, the patient's respiratory rate may be measured based on the outputs of one or more of pressure sensors 80, e.g., based on changes in the ambient pressure or the pressure in the source cavity (e.g., peritoneal, plural, or pericardial cavity) caused by the diaphragm periodically compressing that cavity during breathing.

In a preferred embodiment, processor 70 is programmed to pump fluid from the source cavity to the sink cavity only when the pressure in the source cavity exceeds a first predetermined value, and the pressure in the sink cavity is less than a second predetermined value. To account for patient travel from a location at sea level to a higher altitude, the ambient pressure measurement may be used to calculate a differential value for the peritoneal pressure. In this way, the predetermined pressure at which the pump begins operation may be reduced, to account for lower atmospheric pressure. Likewise, the ambient pressure may be used to adjust the predetermined value for bladder pressure. In this way, the threshold pressure at which the pumping ceases may be reduced, because the patient may experience bladder discomfort at a lower pressure when at a high altitude location.

Referring now to FIGS. 5A and 5B, further details of an exemplary embodiment of implantable device 90 are provided. In FIG. 5A, housing 91 is shown as transparent, although it should of course be understood that housing 91 comprises opaque biocompatible plastic and/or metal alloy materials. In FIG. 5B, the implantable device is shown with lower portion 92 of housing 91 removed from upper housing 93 and without a glass bead/epoxy filler material that is used to prevent moisture from accumulating in the device. In FIGS. 5A and 5B, motor 94 is coupled to gear pump housing 95, which is described in greater detail with respect to FIGS. 6 and 7. The electronic components discussed above with respect to FIG. 4 are disposed on flexible circuit board substrate 96, which extends around and is fastened to support member 97. Coil 98 (corresponding to coil 84 of FIG. 4) is disposed on flap 99 of the substrate and is coupled to the electronic components on flap 100 by flexible cable portion 101. Support member 97 is fastened to upper housing 93 and provides a cavity that holds battery 102 (corresponding to battery 74 of FIG. 4). Lower portion 92 of housing 91 includes port 103 for injecting the glass bead/epoxy mixture after upper portion 93 and lower portion 92 of housing 91 are fastened together, to reduce space in the housing in which moisture can accumulate.

Housing 91 also may include features designed to reduce movement of the implantable pump once implanted within a patient, such as a suture hole to securely anchor the implantable device to the surrounding tissue. Housing 91 may in addition include a polyester ingrowth patch that facilitates attachment of the implantable device to the surrounding tissue following subcutaneous implantation.

Additionally, the implantable device optionally may incorporate anti-clogging agents, such enzyme eluting materials that specifically target the proteinaceous components of ascites, enzyme eluting materials that specifically target the proteinaceous and encrustation promoting components of urine, chemical eluting surfaces, coatings that prevent adhesion of proteinaceous compounds, and combinations thereof. Such agents, if provided, may be integrated within or coated upon the surfaces of the various components of the system.

Referring now to FIGS. 6A to 6D, further details of the gear pump and fluid path are described. In FIGS. 6A-6D, like components are identified using the same reference numbers from FIGS. 5A and 5B. FIG. 6A is an exploded view showing assembly of motor 94 with gear pump housing 95 and upper housing 93, as well as the components of the fluid path within the implantable device. Upper housing 93 preferably comprises a high strength plastic or metal alloy material that can be molded or machined to include openings and channels to accommodate inlet nipple 102, outlet nipple 103, pressure sensors 104a-104d, manifold 105 and screws 106. Nipples 102 and 103 preferably are machined from a high strength biocompatible metal alloy, and outlet nipple 103 further includes channel 107 that accepts elastomeric duckbill valve 108. Outlet nipple 103 further includes lateral recess 109 that accepts pressure sensor 104a, which is arranged to measure pressure at the inlet end of the outflow catheter, corresponding to pressure in the patient's bladder (or peritoneal cavity).

Referring now also to FIGS. 6B and 6C, inlet nipple 102 is disposed within opening 110, which forms a channel in upper housing 93 that includes opening 111 for pressure sensor 104b and opening 112 that couples to manifold 105. Pressure sensor 104b is arranged to measure the pressure at the outlet end of the inflow catheter, corresponding to pressure in the peritoneal (or pleural or pericardial) cavity. Outlet nipple 103, including duckbill valve 107, is disposed within opening 113 of upper housing 93 so that lateral recess 108 is aligned with opening 114 to permit access to the electrical contacts of pressure sensor 104a. Opening 113 forms channel 115 that includes opening 116 for pressure sensor 104c, and opening 117 that couples to manifold 105. Upper housing 93 preferably further includes opening 118 that forms a channel including opening 119 for accepting pressure sensor 104d. Pressure sensor 104d measures ambient pressure, and the output of this sensor is used to calculate differential pressures as described above. Upper housing further includes notch 120 for accepting connector 26 (see FIG. 1) for retaining the inflow and outflow catheters coupled to inlet and outlet nipples 102 and 103. Upper housing 93 further includes recess 121 to accept manifold 105, and peg 122, to which support member 97 (see FIG. 5B) is connected.

As shown in FIGS. 6A and 6D, manifold 105 preferably comprises a molded elastomeric component having two separate fluid channels that couple inlet and outlet flow paths through upper housing 93 to the gear pump. The first channel includes inlet 124 and outlet 125, while the second channel includes inlet 126 and outlet 127. Inlet 124 couples to opening 112 (see FIG. 6C) of the inflow path and outlet 127 couples to opening 117 of the outflow path. Manifold 105 is configured to improve manufacturability of the implantable device, by simplifying construction of upper housing 93 and obviating the need to either cast or machine components with complicated non-linear flow paths.

Figure 7A:
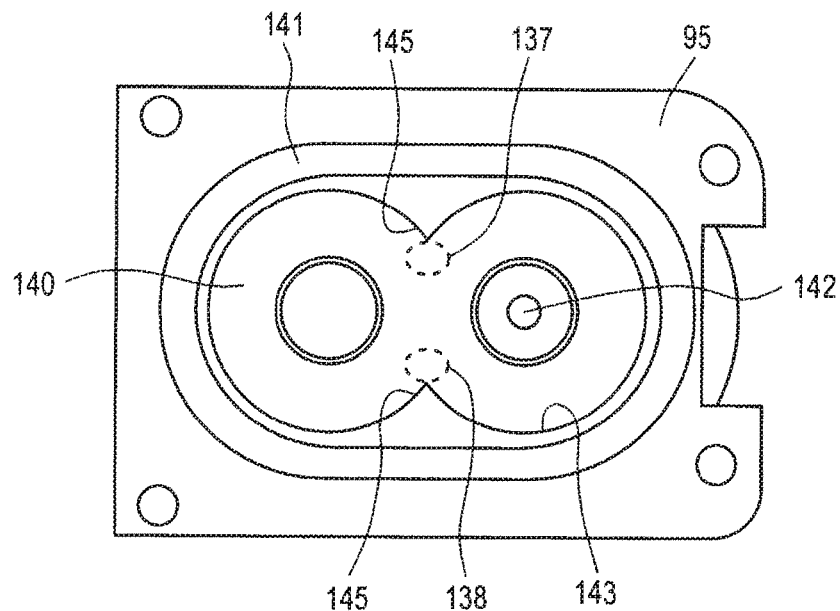
FIGS. 7A and 7B are, respectively, a plan view of the gear pump housing of the implantable device of FIG. 5A, and a plan view of a model of the gear pump constructed in accordance with the principles of the present invention.
Figure 7B:
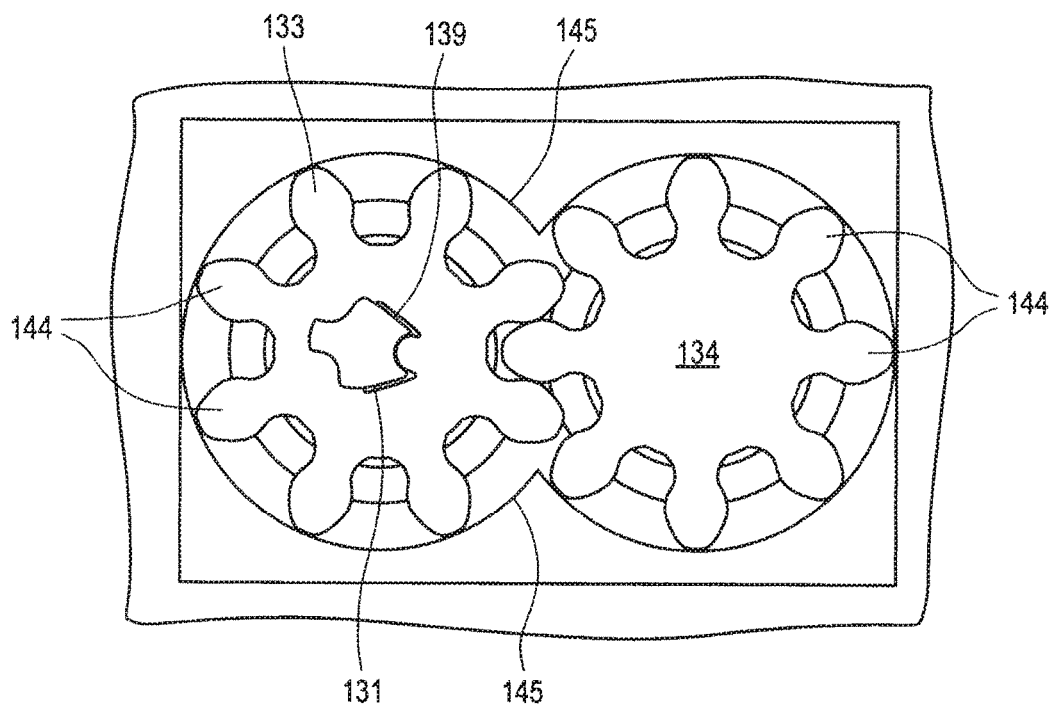

Referring now to FIGS. 6A, 7A and 7B, motor 94 is coupled to gear pump housing 95 using mating threads 130, such that splined shaft 131 of motor 94 passes through bearing 132. The gear pump of the present invention comprises intermeshing gears 133 and 134 enclosed in gear pump housing 95 by O-ring seal 135 and plate 136. The gear pump is self-priming. Plate 136 includes openings 137 and 138 that mate with outlet 125 and inlet 126 of manifold 105, respectively. Splined shaft 131 of motor 94 extends into opening 139 of gear 133 to provide floating engagement with that gear. Interaction of the splined shaft with the gears is described below with respect to FIG. 7B.

FIG. 7A depicts the obverse side of gear pump housing 95 of FIG. 6A, and includes recess 140 that is sized to accept gears 133 and 134, and groove 141 that accepts O-ring seal 135. Gears 133 and 134 are seated within recess 140 such that splined shaft 131 extends through opening 142 and floats within keyed opening 139 of gear 133. Gears 133 and 134 are dimensioned so as to sit within recess 140 with a close tolerance (e.g., 0.2 mm) to wall 143 of the recess, but spin as freely as the viscosity of the fluid permits. Openings 137 and 138 of plate 136 (see FIG. 6A) are positioned over the juncture of gears 133 and 134 (shown in dotted line in FIG. 7A) so that rotation of gear 133 in a clockwise direction (when viewed from above) creates suction that draws fluid into the gear pump housing through opening 137, and expels fluid through opening 138. Likewise, if motor 94 drives gear 133 in a counterclockwise direction (as viewed from above), the gear pump will draw fluid into the gear pump housing through opening 138 and expel it through opening 137, thereby reversing flow.

As depicted in the simplified model of FIG. 7B, gear 134 has no axle, but instead floats freely within its portion of recess 140. Splined shaft 131 engages keyed opening 139 of gear 133, so that gear 133 floats on splined shaft 131. Advantageously, this arrangement improves pump efficiency and manufacturability, and reduces power consumption by motor 94 by reducing the effects of manufacturing variations and thermal effects. In particular, slight variations in motor shaft eccentricity or straightness, resulting from manufacturing tolerances or differential thermal expansion, will not cause the gear to bind against the interior of recess 140 or against gear 134. Instead, different portions of the surfaces of shaft 131 and keyed opening 139 contact one another during revolution of shaft 131 to continuously transmit rotational torque to gear 133. However, energy-wasting forces resulting from shaft eccentricities, variations in manufacturing tolerances or differential thermal expansion of the components are reduced. In addition, this floating arrangement may reduce the risk that particulate matter causes binding between the gears and wall 143, since the gears may move laterally to accommodate such particulate matter.

Gears 133 and 134 include intermeshing lobes 144 that positively displace fluid as they engage and disengage, with substantially no bypass flow. In this manner the volume and viscosity of fluid transported by gears 133 and 134 may computed by tracking the number of motor revolutions sensed by the Hall Effect sensors disposed within motor 94. As further shown in FIGS. 7A and 7B, recess 140 of gear pump housing 95 comprises two interconnected, substantially circular, lobes. This arrangement retains gears 133 and 134 in proper relation to wall 143 of the recess, as well as relative to one another. In a preferred embodiment, cusps 145, formed where the two lobes intersect, are configured to form tangents to radii drawn from the centers of the respective lobes. Advantageously, configuring the cusps in this manner reduces the potential for gears 133 and 134 to impinge upon wall 143.

The Charging and Communication System

Figure 8A:
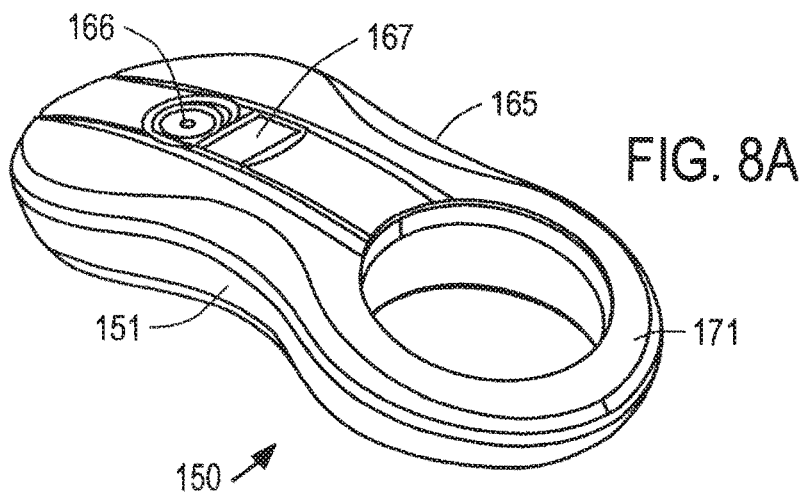
FIGS. 8A and 8B are, respectively, perspective and top views of the handpiece portion of an exemplary charging and communication system of the present invention.
Figure 8B:
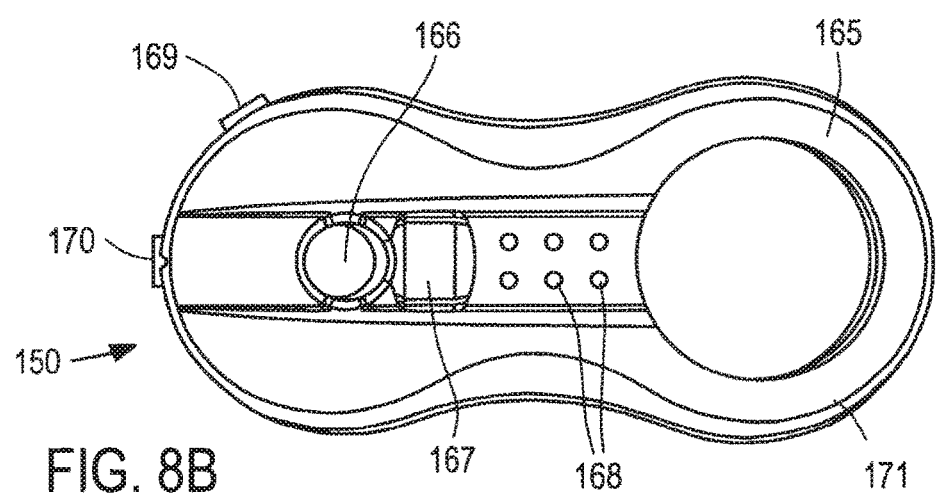
Figure 9:
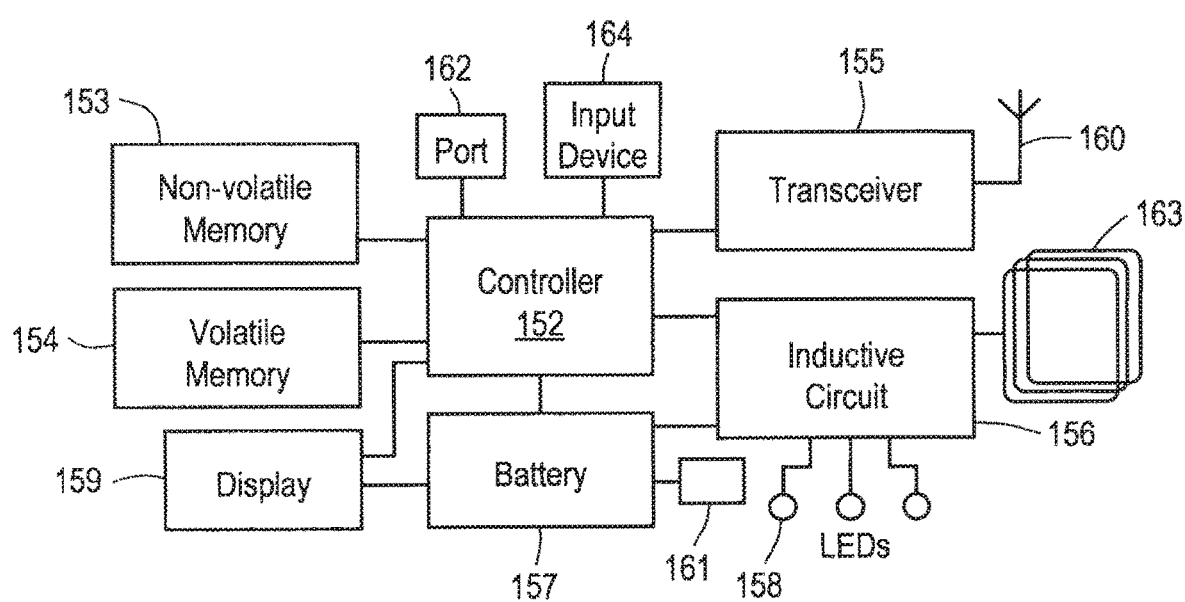
FIG. 9 is a schematic diagram of the electronic components of an exemplary embodiment of the charging and communication system of the present invention.

Referring to FIGS. 8A, 8B and 9, charging and communication system 150 of the present invention (corresponding to system 30 of FIG. 1) is now described in greater detail. In one preferred embodiment, charging and communication system 150 comprises handpiece 151 and base 31 (see FIG. 1). Base 31 provides comprises a cradle for recharging handpiece 151, and preferably contains a transformer and circuitry for converting conventional 120V power service to a suitable DC current to charge handpiece 151 when it is coupled to the base. Alternatively, handpiece 151 may include circuitry for charging the handpiece battery, and a detachable power cord. In this embodiment, handpiece 151 may be directly plugged into a convention 120V wall socket for charging, and the power cord removed when the handpiece is used to recharge the implantable device.

As shown in FIG. 9, handpiece 151 contains controller 152, illustratively the processor of a micro-controller unit coupled to nonvolatile memory 153 (e.g., either EEPROM or flash memory), volatile memory 154, radio transceiver 155, inductive circuit 156, battery 157, indicator 158 and display 159. Controller 152, memories 153 and 154, and radio transceiver 155 may be incorporated into a single microcontroller unit, such as the MPS430 family of microprocessors, available from Texas Instruments Incorporated, Dallas, Tex. Transceiver 155 is coupled to antenna 160 for sending and receiving information to implantable device 20. Battery 157 is coupled to connector 161 that removably couples with a connector in base 31 to recharge the battery. Port 162, such as a USB port or comparable wireless circuit, is coupled to controller 152 to permit information to be exchanged between handpiece 151 and the monitoring and control system. Inductive circuit 156 is coupled to coil 163. Input device 164, preferably a multi-function button, also is coupled to controller 152 to enable a patient to input a limited number of commands. Indicator 158 illustratively comprises a plurality of LEDs that illuminate to indicate the quality of charge coupling achieved between the handpiece and implantable device, and therefore assist in optimizing the positioning of handpiece 151 relative to the implantable device during recharging. In one preferred embodiment, indicator 158 is omitted, and instead a bar indicator provided on display 159 that indicates the quality-of-charging resulting from the coupling of coils 163 and 84.

In a preferred embodiment, handpiece 151 includes a device identifier stored in nonvolatile memory 153 that corresponds to the device identifier stored in nonvolatile memory 71 of the implantable device, such that handpiece 151 will communicate only with its corresponding implantable device 20. Optionally, a configurable handpiece for use in a physician's office may include the ability to interrogate an implantable device to request that device's unique device identifier, and then change the device identifier of the monitoring and control system 40 to that of the patient's implantable device, so as to mimic the patient's handpiece. In this way, a physician may adjust the configuration of the implantable device if the patient forgets to bring his handpiece 151 with him during a visit to the physician's office.

Controller 152 executes firmware stored in nonvolatile memory 153 that controls communications and charging of the implantable device. Controller 152 also is configured to transfer and store data, such as event logs, uploaded to handpiece 151 from the implantable device, for later retransmission to monitoring and control system 40 via port 162, during physician office visits. Alternatively, handpiece 151 may be configured to recognize a designated wireless access point within the physician's office, and to wirelessly communicate with monitoring and control system 40 during office visits. As a further alternative, base 31 may include telephone circuitry for automatically dialing and uploading information stored on handpiece 151 to a physician's website via a secure connection, such as alarm information.

Controller 152 preferably includes a low-power mode of operation and includes an internal clock, such that the controller periodically awakens to communicate with the implantable device to log data or to perform charging functions. Controller 152 preferably is configured to awaken when placed in proximity to the implantable device to perform communications and charging functions, and to transmit commands input using input device 164. Controller 152 further may includes programming for evaluating information received from the implantable device, and generating an alarm message on display 159. Controller 152 also may include firmware for transmitting commands input using input device 164 to the implantable device, and monitoring operation of the implantable device during execution of such commands, for example, during boost or jogging/shaking operation of the gear pump to clear a blockage. In addition, controller 152 controls and monitors various power operations of handpiece 151, including operation of inductive circuit 156 during recharging of the implantable device, displaying the state of charge of battery 74, and controlling charging and display of state of charge information for battery 157.

Nonvolatile memory 153 preferably comprises flash memory or EEPROM, and stores the unique device identifier for its associated implantable device, firmware to be executed by controller 152, configuration set point, and optionally, coding to be executed on transceiver 155 and/or inductive circuit 156. Firmware and set point data stored on nonvolatile memory 153 may be updated using information supplied by control and monitoring system 40 via port 162. Volatile memory 154 is coupled to and supports operation of controller 152, and stores data and event log information uploaded from implantable device 20.

In addition, in a preferred embodiment, nonvolatile memory 153 stores programming that enables the charging and communication system to perform some initial start-up functions without communicating with the monitor and control system. In particular, memory 153 may include routines that make it possible to test the implantable device during implantation using the charging and communication system alone in a "self-prime mode" of operation. In this case, a button may be provided that allows the physician to manually start the pump, and display 159 is used to provide feedback whether the pumping session was successful or not. Display 159 of the charging and communication system also may be used to display error messages designed to assist the physician in adjusting the position of the implantable device or inflow or outflow catheters. These functions preferably are disabled after the initial implantation of the implantable device.

Transceiver 155 preferably comprises a radio frequency transceiver, e.g., conforming to the Bluetooth or IEEE 802.11 wireless standards, and is configured for bi-directional communications via antenna 160 with transceiver circuit 76 disposed in the implantable device. Transceiver 155 also may include a low power mode of operation, such that it periodically awakens to listen for incoming messages and responds only to those messages including the unique device identifier assigned to its associated implantable device. Transceiver 155 preferably employs an encryption routine to ensure that messages sent to, or received from, the implantable device cannot be intercepted or forged.

Inductive circuit 156 is coupled to coil 163, and is configured to inductively couple with coil 84 of the implantable device to recharge battery 74 of the implantable device. In one embodiment, inductive circuit 156 is coupled to indicator 158, preferably a plurality of LEDs that light to indicate the extent of magnetic coupling between coils 163 and 84 (and thus quality of charging), thereby assisting in positioning handpiece 151 relative to the implantable device. In one preferred embodiment, inductive coils 84 and 163 are capable of establishing good coupling through a gap of 35 mm, when operating at a frequency of 315 kHz or less. In an embodiment in which implantable device includes optional infrared LED 83, charging and communication system 30 may include an optional infrared sensor (not shown) which detects that infrared light emitted by LED 83 and further assists in positioning handpiece 151 to optimize magnetic coupling between coils 163 and 84, thereby improving the energy transmission to the implantable device.

In accordance with one aspect of the present invention, controller 152 may be configured to periodically communicate with the implantable device to retrieve temperature data generated by temperature sensor 78 and stored in memory 72 during inductive charging of battery 74. Controller 152 may include firmware to analyze the battery temperature, and to adjust the charging power supplied to inductive circuit 163 to maintain the temperature of the implantable device below a predetermined threshold, e.g., less than 2° C. above body temperature. That threshold may be set to reduce thermal expansion of the battery and surrounding electronic and mechanical components, for example, to reduce thermal expansion of motor and gear pump components and to reduce the thermal strain applied to the seal between lower portion 92 of housing and upper housing 93. In a preferred embodiment, power supplied to inductive coil 163 is cycled between high power (e.g., 120 mA) and low power (e.g., 40 mA) charging intervals responsive to the measured temperature within the implantable device.

As discussed above with respect to inductive circuit 75 of the implantable device, inductive circuit 156 optionally may be configured to transfer additional power to motor 73 of the implantable device, via inductive circuit 75 and battery 74, in a "boost" mode or jogging mode to unblock the gear pump. In particular, if an alarm is transmitted to controller 152 that motor 73 is stalled, e.g., due to a block created by ascitic fluid, the patient may be given the option of using input device 164 to apply an overvoltage to motor 73 from inductive circuit 75 for a predetermined time period to free the blockage. Alternatively, activating input device 164 may cause controller 152 to command processor 70 to execute a routine to jog or shake the gear pump by rapidly operating motor 74 in reverse and forward directions to disrupt the blockage. Because such modes of operation may employ higher energy consumption than expected during normal operation, inductive circuits 156 and 75 may be configured to supply the additional energy for such motor operation directly from the energy stored in battery 157, instead of depleting battery 74 of the implantable device.

Battery 157 preferably comprises a lithium ion or lithium polymer battery capable of long lasting operation, e.g., up to three years. Battery 157 has sufficient capacity to supply power to handpiece 151 to operate controller 152, transceiver 155, inductive circuit 156 and the associated electronics while disconnected from base 31 and during charging of the implantable device. In a preferred embodiment, battery 157 has sufficient capacity to fully recharge battery 74 of the implantable device from a depleted state in a period of about 2-4 hours. Battery 157 also should be capable of recharging within about 2-4 hours. It is expected that for daily operation moving 700 ml of fluid, battery 157 and inductive circuit 156 should be able to transfer sufficient charge to battery 74 via inductive circuit 75 to recharge the battery within about 30 minutes. Battery capacity preferably is supervised by controller 152 using a charge accumulator algorithm.

Referring again to FIGS. 8A and 8B, handpiece 151 preferably includes housing 165 having multi-function button 166 (corresponding to input device 164 of FIG. 9) and display 167 (corresponding to display 159 of FIG. 9). Plurality of LEDs 168 is disposed beneath a translucent portion of handpiece 151, and corresponds to indicator 158 of FIG. 9. Port 169 enables the handpiece to be coupled to monitoring and control system 40 (and corresponds to port 162 of FIG. 9), while connector 170 (corresponding to connector 161 in FIG. 9) permits the handpiece to be coupled to base 31 to recharge battery 157. Multi-function button 166 provides the patient the ability to input a limited number of commands to the implantable device. Display 167, preferably an OLED or LCD display, provides visible confirmation that a desired command input using multifunction button 166 has been received. Display 167 also may display the status and state of charge of battery 74 of the implantable device, the status and state of charge of battery 157 of handpiece 151, signal strength of wireless communications, quality-of-charging, error and maintenance messages. Inductive coil portion 171 of housing 165 houses inductive coil 163.

LEDs 168 are visible through the material of housing 165 when lit, and preferably are arranged in three rows of two LEDs each. During charging, the LEDs light up to display the degree of magnetic coupling between inductive coils 163 and 84, e.g., as determined by energy loss from inductive circuit 156, and may be used by the patient to accurately position handpiece 151 relative to the implantable device. Thus, for example, a low degree of coupling may correspond to lighting of only two LEDs, an intermediate degree of coupling with lighting of four LEDs, and a preferred degree of coupling being reflected by lighting of all six LEDs. Using this information, the patient may adjust the position of handpiece 151 over the area where implantable device is located to obtain a preferred position for the handpiece, resulting in the shortest recharging time. In one preferred embodiment, LEDs 168 are replaced with an analog bar display on display 167, which indicates the quality of charge coupling.

The Monitoring and Control System

Figure 10:
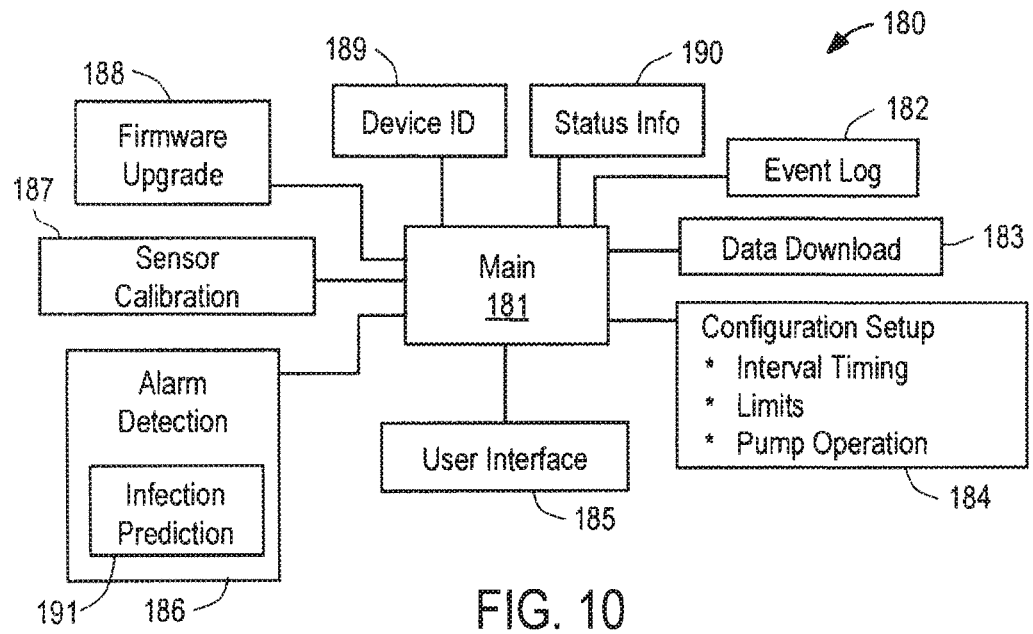
FIG. 10 is a schematic diagram of the functional components of the monitoring and control software employed in an exemplary embodiment of the fluid management system of the present invention.

Turning to FIG. 10, the software implementing monitoring and control system of FIG. 1 now described. Software 180 comprises a number of functional blocks, schematically depicted in FIG. 10, including main block 184, event logging block 182, data download block 183, configuration setup block 184, user interface block 185, alarm detection block 186 including infection prediction block 191, sensor calibration block 187, firmware upgrade block 188, device identifier block 189 and status information block 190. The software preferably is written in C++ and employs an object oriented format. In one preferred embodiment, the software is configured to run on top of a Microsoft Windows® (a registered trademark of Microsoft Corporation, Redmond, Wash.) or Unix-based operating system, such as are conventionally employed on desktop and laptop computers. The computer running monitoring and control system software 180 preferably includes a data port, e.g., USB port or comparable wireless connection, that permits handpiece 151 of the charging and communication system to be coupled via port 169. Alternatively, as discussed above, the computer may include a wireless card, e.g., conforming to the IEEE 802.11 standard, thereby enabling handpiece 151 to communicate wirelessly with the computer running software 180. As a further alternative, the charging and communication system may include telephony circuitry that automatically dials and uploads data, such as alarm data, from handpiece 151 to a secure website accessible by the patient's physician.

Main block 184 preferably consists of a main software routine that executes on the physician's computer, and controls overall operation of the other functional blocks. Main block 184 enables the physician to download event data and alarm information stored on handpiece 151 to his office computer, and also permits control and monitoring software 180 to directly control operation of the implantable device when coupled to handpiece 151. Main block also enables the physician to upload firmware updates and configuration data to the implantable device.

Event Log block 182 is a record of operational data downloaded from the implantable device via the charging and communication system, and may include, for example, pump start and stop times, motor position, sensor data for peritoneal (or pleural or pericardial) cavity and sink cavity (e.g. bladder) pressures, patient temperature, respiratory rate or fluid temperature, pump outlet pressure, humidity, pump temperature, battery current, battery voltage, battery status, and the like. The event log also may include the occurrence of events, such as pump blockage, operation in boost or jog modes, alarms or other abnormal conditions.

Data Download block 183 is a routine that handles communication with handpiece 151 to download data from volatile memory 154 after the handpiece is coupled to the computer running monitoring and control software 180. Data Download block 183 may initiates, either automatically or at the instigation of the physician via user interface block 185, downloading of data stored in the event log.

Configuration Setup block 184 is a routine that configures the parameters stored within nonvolatile memory 71 that control operation of the implantable device. The interval timing parameters may determine, e.g., how long the processor remains in sleep mode prior to being awakened to listen for radio communications or to control pump operation. The interval timing parameters may control, for example, the duration of pump operation to move fluid from the peritoneum (or pleura or pericardial sac) to the sink cavity and the interval between periodic tick movements that prevent blockage of the implantable device and inflow and outflow catheters. Interval timing settings transmitted to the implantable device from monitoring and control software 180 also may determine when and how often event data is written to nonvolatile memory 71, and to configure timing parameters used by the firmware executed by processor 152 of handpiece 151 of the charging and communication system. Block 184 also may be used by the physician to configure parameters stored within nonvolatile memory 71 relating to limit values on operation of processor 70 and motor 73. These values may include minimum and maximum pressures at the inflow and outflow catheters, the maximum temperature differential during charging, times when the pump may and may not operate, etc. The limit values set by block 184 also configure parameters that control operation of processor 152 of handpiece 151. Block 184 also may configure parameters store within nonvolatile memory 71 of the implantable device relating to control of operation of processor 70 and motor 73. These values may include target daily volumes of fluid to transport, volume of fluid to be transported per pumping session, motor speed and duration per pumping session. Block 184 also may specify the parameters of operation of motor 73 during boost mode of operation, when coupled to handpiece 151, and shake/jog modes of operation when the implantable device is run using battery 74 alone. Such parameters may include motor speed and voltage, duration/number of revolutions of the motor shaft when alternating between forward and reverse directions, etc.

User interface block 185 handles display of information retrieved from the monitoring and control system and implantable device via data download block 183, and presents that information in an intuitive, easily understood format for physician review. As described below with respect to FIGS. 11 to 15, such information may include status of the implantable device, status of the charging and control system, measured pressures, volume of fluid transported per pumping session or per day, etc. User interface block 185 also generates user interface screens that permit the physician to input information to configure the interval timing, limit and pump operation parameters discussed above with respect to block 184.

Alarm detection block 186 may include a routine for evaluating the data retrieved from the implantable device or charging and communication system, and flagging abnormal conditions for the physician's attention. For example, alarm detection block 186 may include infection prediction block 191, which is configured to predict or detect infection based on, for example, one or more of an increase in the patient's temperature above a predefined threshold, an increase in the patient's respiratory rate above a predefined threshold, and/or an increase in the fluid above a predefined threshold. Such flags may be communicated to the physician by changing status indicators presented by user interface block 185, or by displaying to the physician specific information about increases in the patient's temperature, respiratory rate, or fluid viscosity via user interface block 185.

Sensor calibration block 187 may include a routines for testing or measuring drift, of sensors 70, 78-81 employed in the implantable device, e.g., due to aging or change in humidity. Block 187 may then compute offset values for correcting measured data from the sensors, and transmit that information to the implantable device for storage in nonvolatile memory 71. For example, pressure sensors 104a-104d may experience drift due to aging or temperature changes. Block 187 accordingly may compute offset values that are then transmitted and stored in the implantable device to account for such drift.

Firmware upgrade block 188 may comprise a routine for checking the version numbers of the processor or motor controller firmware installed on the implantable device and/or processor firmware on charging and communication system, and identify whether upgraded firmware exists. If so, the routine may notify the physician and permit the physician to download revised firmware to the implantable device for storage in nonvolatile memory 71 or to download revised firmware to the charging and communication system for storage in nonvolatile memory 153.

Device identifier block 189 consists of a unique identifier for the implantable device that is stored in nonvolatile memory 71 and a routine for reading that data when the monitoring and control system is coupled to the implantable device via the charging and communication system. As described above, the device identifier is used by the implantable device to confirm that wireless communications received from a charging and communication system are intended for that specific implantable device. Likewise, this information is employed by handpiece 151 of the charging and communication system in determining whether a received message was generated by the implantable device associated with that handpiece. Finally, the device identifier information is employed by monitoring and control software 180 to confirm that the handpiece and implantable device constitute a matched set.

Status information block 190 comprises a routine for interrogating implantable device, when connected via handpiece 151, to retrieve current status date from the implantable device, and/or handpiece 151. Such information may include, for example, battery status, the date and time on the internal clocks of the implantable device and handpiece, version control information for the firmware and hardware currently in use, and sensor data.

Figure 11:
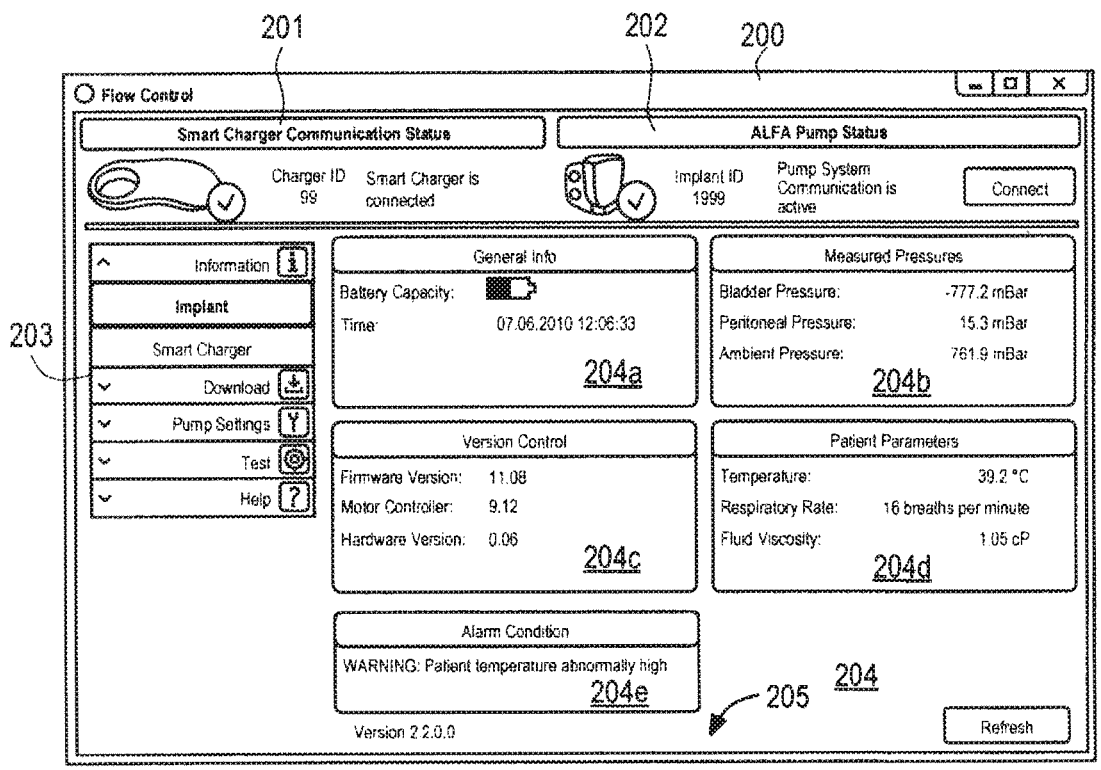
FIGS. 11-15 are exemplary screenshots illustrating various aspects of the user interface of the monitoring and control system of the present invention.

Referring now to FIGS. 11-15, exemplary screen shots generated by user interface block 187 of software 180 are described for an ascites treatment system. FIG. 11 shows main screen 200 that is displayed to a physician running monitoring and control software 180. Main screen 200 includes a status area that displays status information retrieved from the implantable device and the charging and communication system by the routine corresponding to block 190 of FIG. 10. More particularly, the status area includes status area 201 for the charging and communication system (referred to as the "Smart Charger) and status area 202 for the implantable device (referred to as the "ALFA Pump"). Each status area includes an icon showing whether the respective system is operating properly, indicated by a checkmark, the device identifier for that system, and whether the system is connected or active. If a parameter is evaluated by the alarm detection block 186 to be out of specification, the icon may instead include a warning symbol. Menu bar 203 identifies the various screens that the physician can move between by highlighting the respective menu item. Workspace area 204 is provided below the status area, and includes a display that changes depending upon the menu item selected. Below workspace area 204, navigation panel 205 is displayed, which includes the version number of software 180 and a radio button that enables the displays in workspace area 204 to be refreshed.

In FIG. 11, the menu item "Information" with submenu item "Implant" is highlighted in menu bar 203. For this menu item selection, workspace area 204 illustratively shows, for the implantable device, battery status window 204a, measured pressures window 204b and firmware version control window 204c. Battery status window 204a includes an icon representing the charge remaining in battery 74, and may be depicted as full, three-quarters, one-half, one-quarter full or show an alarm that the battery is nearly depleted. The time component of window 204a indicates the current time as received from the implantable device, where the date is expressed in DD/MM/YYYY format and time is expressed in RR/MIN/SEC format based on a 24 hour clock. Measured pressures window 204b displays the bladder pressure, peritoneal pressure and ambient pressures in mBar measured by sensors 104a, 104b and 104d respectively (see FIG. 6A). Version control window 204c indicates the firmware version for processor 70, for the motor controller, and the hardware version of the implantable device. Patient parameters window 204d displays the patient's temperature, respiratory rate, and fluid viscosity. Alarm condition window 204e displays any changes in parameters that may indicate the possible development of an infection (block 191 in FIG. 10). For example, as illustrated, alarm condition window 204e may alert the physician that the patient's temperature is abnormally high, so that the physician then may follow up with the patient regarding the possibility of infection. In some embodiments, based on information displayed in windows 204b, 204d, and/or 204e, the physician may adjust the operating parameters of the pump, e.g., using the interface described below with reference to FIG. 14.

Figure 12:
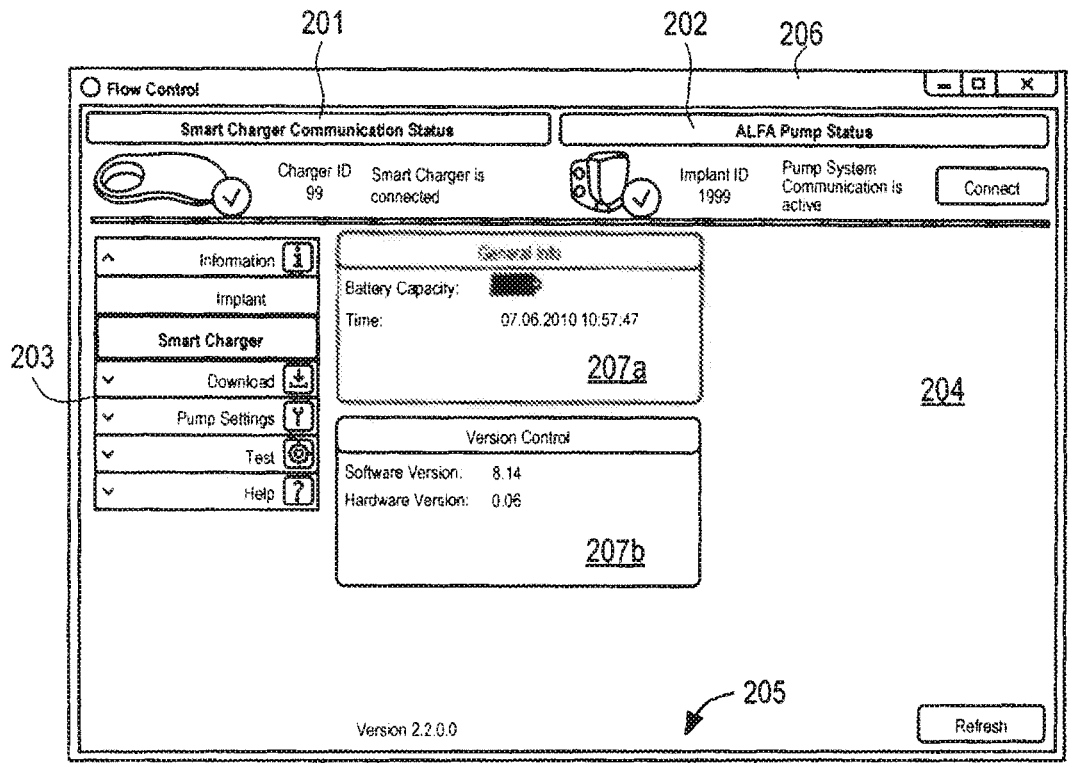

Turning to FIG. 12, screen display 206 corresponding to selection of the "Smart Charger" submenu item in FIG. 11 is described. FIG. 12 includes status area 201 for the charging and communication system, status area 202 for the implantable device, menu bar 203, workspace area 204, and navigation panel 205 as discussed above with respect to FIG. 11. Screen display 206 differs from screen display 200 in that the "Smart Charger" submenu item is highlighted, and workspace area 204 displays, for the charging and control system, battery status window 207a and version control window 207b. Battery status window 207a includes an icon representing the charge remaining in battery 157, and may be depicted as full, three-quarters, one-half, one-quarter full or show an alarm that the battery is nearly depleted. The time component of window 207a indicates the current time as received from handpiece 151, where the date is expressed in DD/MM/YYYY format and time is expressed in RR/MIN/SEC format based on a 24 hour clock. Version control window 207b indicates the firmware version for processor 152, and the hardware version of the charging and control system.

Figure 13:
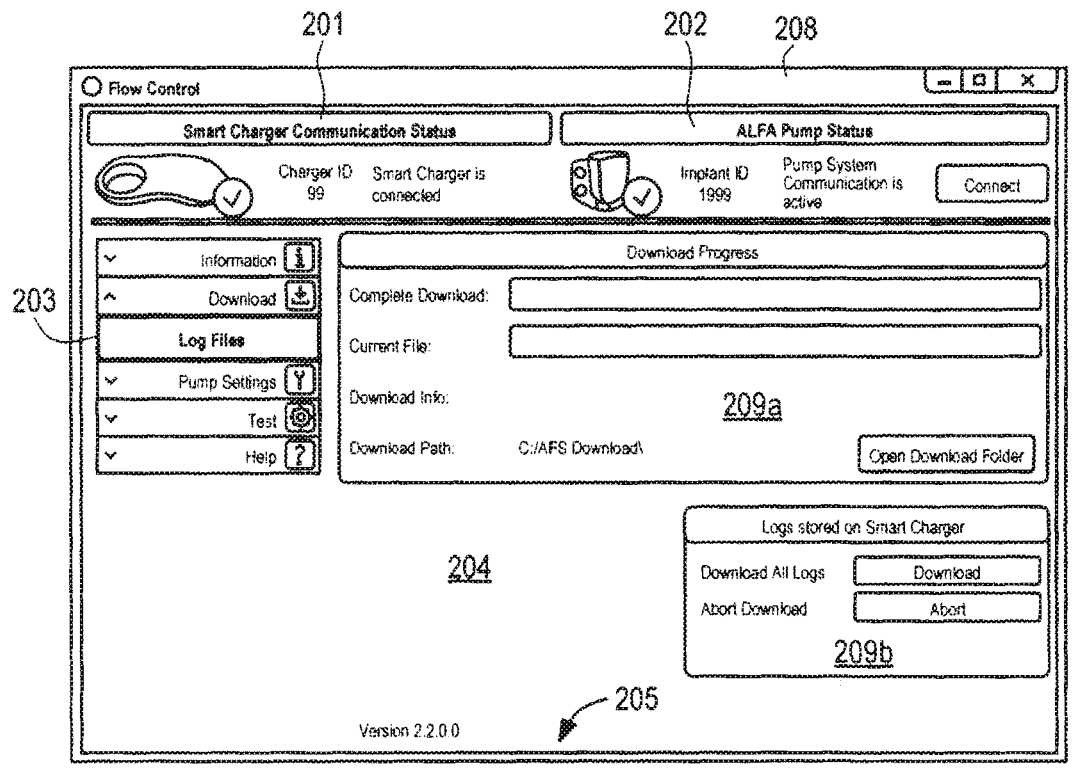

Referring now to FIG. 13, screen display 208 corresponding to selection of the "Download" menu item in FIG. 11 and "Log Files" submenu item is described, and implements the functionality of block 183 of software 180. FIG. 13 includes status area 201 for the charging and communication system, status area 202 for the implantable device, menu bar 203, workspace area 204, and navigation panel 205, all as discussed above. Screen display 208 differs from the "Information" screen display in that the "Log Files" submenu item is highlighted, and workspace area 204 displays download progress window 209a and storage path window 209b. Window 209a includes the path for the directory to which event logs may be downloaded from the implantable device via the charging and communication system. Window 209a also includes an "Open Download Folder" radio button that allows the physician to choose the directory path to which the event logs are downloaded, and a progress bar that is updated to reflect the amount of data downloaded. Window 209b includes a radio button that can be activated to download the event log to the path specified in window 209a, and also includes an "Abort" radio button to interrupt the download process.

Figure 14:
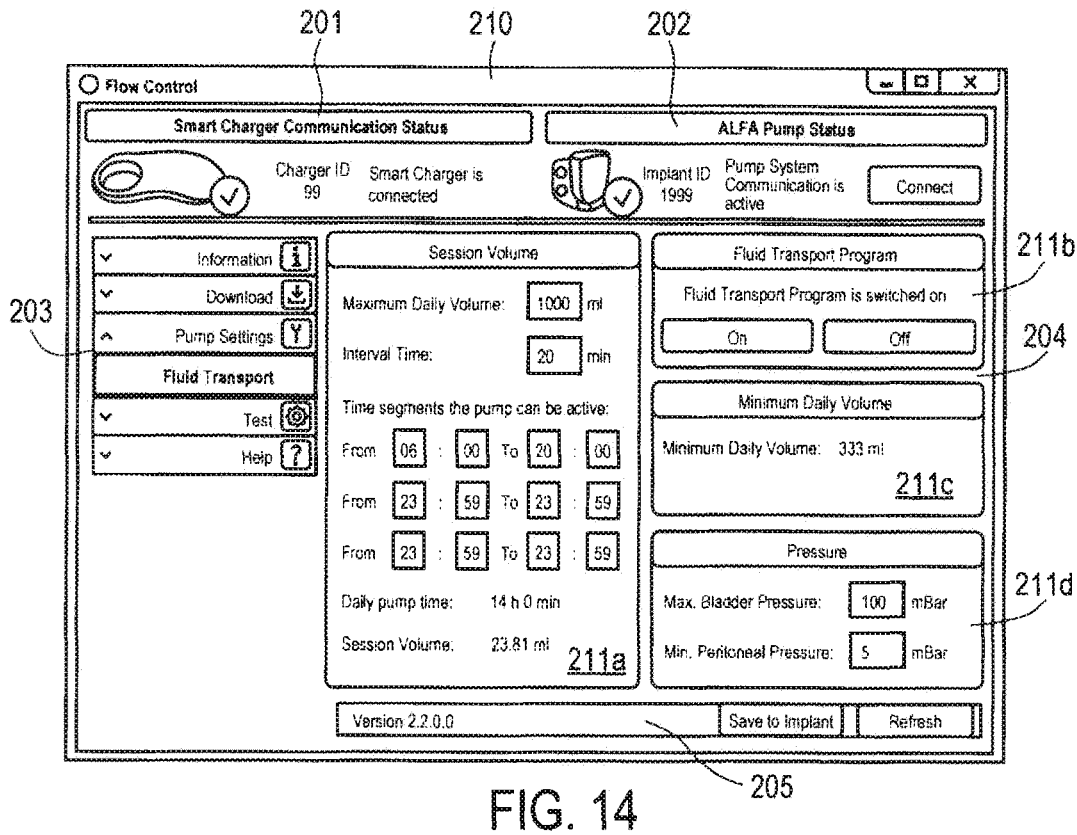

FIG. 14 is an exemplary depiction of screen display 210, corresponding to selection of the "Pump Settings" menu item in FIG. 11 and "Fluid Transport" submenu item, and implements the functionality of blocks 184 and 190 of software 180. FIG. 14 includes status area 201 for the charging and communication system, status area 202 for the implantable device, menu bar 203, workspace area 204, and navigation panel 205, all as discussed above. Screen display 210 differs from the "Information" screen displays in that the "Fluid Transport" submenu item is highlighted, and workspace area 204 includes session volume window 211a, fluid transport program window 211b, minimum daily volume window 211c, pressure window 211d, and a radio button in navigation panel 205 that permits values entered in windows 211a, 211b and 211d to be transmitted and stored in non-volatile memory 71 of the implantable device. Session volume window 211a displays the current setting for the maximum daily volume to be pumped by the implantable device, the interval time between pumping sessions, the times of the day that the pump may be activated, the total daily pump time and the session volume per pumping session.

The maximum daily volume displayed in window 211a corresponds to the upper limit of fluid that the pump will transfer to the bladder in a 24-hour period, although the actual volume pumped may be lower if the implantable device detects low fluid conditions. This value is based on patient general status and daily ascites production, and may have an allowed range, e.g., of 20 ml to 4000 ml. The interval time displayed in window 211a is used by the configuration setup routine (block 184 of FIG. 10) to compute the session volume, which preferably is in a range of 3 ml to 30 ml, and more preferably in a range of 10 ml to 20 ml. The time segments that the pump may be active, displayed in window 211a, define the timeframes during which the implantable device can actively move fluid to the bladder; outside of these time segments, the implantable device will not move fluid but may implement the pump tick operation described above to turn the gears on a regular basis to prevent clogging of the gears. The daily pump time displayed in window 211a is shown in read-only format because it is the aggregate of the time segments entered in the time segments boxes. Finally, the session volume displayed in window 211a is computed by block 183 as the amount of fluid transferred to the bladder in a single pumping session.

Fluid transport program window 211b displays the status of the program controlling operation of the pump of the implantable device based on the parameters set using block 184 of software 180. In case pump activity must be stopped for any reason, the fluid transport program can be stopped by clicking the "Off" button in window 211b, which will cause the Pump to stop pumping until it is manually switched back on. In one embodiment, the fluid transport program may switched on again by pressing the "On" button in window 211b. Because the implantable device preferably is implanted with the pump turned off, the physician or surgeon may use window 211b to turn on the fluid transport program after the implantable device is first implanted.

Minimum daily volume window 211c displays the expected amount of fluid to be pumped to the bladder by the implantable device, and is computed by the configuration setup routine as the session volume times the number of sessions per day, based on the length of the prescribed time segments and interval timing input in window 211a.

Pressure window 211d of FIG. 14 permits the physician to input values of maximum bladder pressure and minimum peritoneal pressure that are used to control operation of the implantable pump. Thus, for example, processor 70 will command motor 73 to cease a current pumping session, or to skip a planned pumping session during the time segments identified in window 211a, if the bladder pressure detected by the pressure sensors exceeds the value specified in window 211d. Likewise, processor 70 will command motor 73 to cease a current pumping session, or to skip a planned pumping session during the time segments identified in window 211a, if the peritoneal pressure detected by the pressure sensors is less than the value specified in window 211d. If configured to operate in the above-described manner, the implantable device will neither cause patient discomfort by overfilling the patient's bladder, nor cause the peritoneal, pleural or pericardial cavity to become excessively dry.

Figure 15:
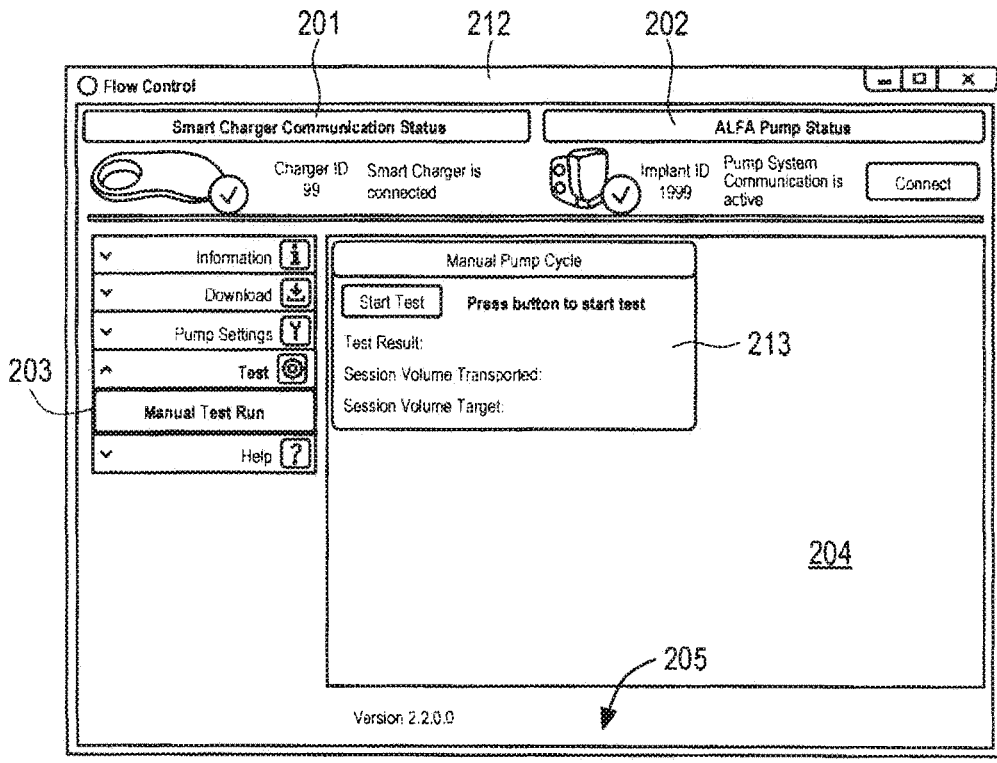

Referring now to FIG. 15, an exemplary depiction of screen display 212, corresponding to selection of the "Test" menu item in FIG. 11 and "Manual Test Run" submenu item is described. FIG. 15 includes status area 201 for the charging and communication system, status area 202 for the implantable device, menu bar 203, workspace area 204, and navigation panel 205, all as discussed above. Screen display 212 differs from the "Information" screen displays in that the "Manual Test Run" submenu item is highlighted, and workspace area 204 includes manual pump cycle window 213. Manual pump cycle window 213 includes radio button "Start Test" which transmits a command to the implantable device via the charging and communication system to cause processor 70 to activate the pump for a predetermined period of time, e.g., a few seconds. Processor 70 receives positional data from the Hall Effect sensors in motor 73 and measured pressure data across pressure sensors 104c and 104d. Processor 70 computes a session volume and relays that information via the charging and communication system back to software 10, which compares the measured data to a target session volume and provides a test result, e.g., percentage of session target volume achieved or pass/fail icon. The measured session volume, session target volume and test result are displayed in window 213.

Although the exemplary embodiment described above relates to a fluid management system for treating chronic ascites, the fluid management system of the present invention may be readily adapted for use in treating pleural or pericardial effusion. In such embodiments, it would be advantageous to account for fluctuations in the pressure in the pleural or pericardial cavities arising due to respiration or normal cardiac activity, to avoid draining all fluid from the cavity and interfering with proper lung function or cardiac activity. For a fluid management system intended for treatment of pleural effusion, this may be accomplished, for example, by programming processor 70 of the implantable device to measure pressure in the pleural cavity over the course of the respiratory cycle. This information may then be used to compute a mean pressure that is used to determine when to cease pumping fluid from the pleural cavity. Likewise, for a fluid management system of the present invention intended for treatment of pericardial effusion, processor 70 of the implantable device may be programmed to measure pressure in the pericardial cavity over the course of the cardiac cycle. This information may then be used to compute a mean pressure that is used to determine when to cease pumping fluid from the pericardial sac, so as to ensure some fluid remains to lubricate heart motion within the pericardial sac due to normal cardiac activity.

While various illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A fluid management system comprising:
    an inflow catheter comprising an inlet end and an outlet end, the inlet end in fluid communication with a first cavity;
    an outflow catheter comprising an inlet end and an outlet end, the outlet end in fluid communication with a second cavity; and
    an implantable device coupled to the outlet end of the inflow catheter and the inlet end of the outflow catheter, the implantable device comprising a housing containing a battery, at least one sensor, a processor in electrical communication with the at least one sensor, and a positive displacement gear pump coupled to an electric motor, the at least one sensor configured to sense positional data and a direction of rotation of the electric motor, and the processor configured to receive at least one signal indicative of the positional data and the direction of rotation of the electric motor sensed by the at least one sensor and to process the at least one signal to generate information indicative of a volume of fluid pumped by the implantable device.

2. The fluid management system of claim 1, wherein the at least one sensor comprises at least one hall effect sensor.

3. The fluid management system of claim 1, wherein the positional data of the electric motor processed by the processor comprises information on a degree of rotation of the positive displacement gear pump.

4. The fluid management system of claim 1, wherein the processor is configured to process the at least one signal to generate information indicative of a flow rate of fluid pumped by the implantable device.

5. The fluid management system of claim 1, wherein the processor is configured to process the at least one signal to generate information indicative of a viscosity of fluid pumped by the implantable device.

6. The fluid management system of claim 1, wherein the inlet end of the inflow catheter is in fluid communication with the first cavity that is one of the following: a peritoneal cavity, a pleural cavity, or a pericardial cavity.

7. The fluid management system of claim 1, wherein the outlet end of the outflow catheter is in fluid communication with the second cavity that is a bladder or a peritoneal cavity.

8. The fluid management system of claim 1, further comprising a charging and communication system in wireless communication with the implantable device, the charging and communication system configured to charge the battery.

9. The fluid management system of claim 8, wherein the charging and communication system is configured to receive the information indicative of the volume of fluid pumped from the implantable device.

10. The fluid management system of claim 9, further comprising monitoring and control software in communication with the charging and communication system, the monitoring and control software configured to permit control of operational parameters of the implantable device and receive the information indicative of the volume of fluid pumped from the charging and communication system.

11. A method for managing fluid in a system, the method comprising:
    providing an inflow catheter comprising an inlet end and an outlet end, the inlet end in fluid communication with a first cavity; an outflow catheter comprising an inlet end and an outlet end, the outlet end in fluid communication with a second cavity;
    pumping, by an implantable device coupled to the outlet end of the inflow catheter and the inlet end of the outflow catheter, fluid from the first cavity to the second cavity; the implantable device comprising a housing containing a battery, at least one sensor, a processor in electrical communication with the at least one sensor, and a positive displacement gear pump coupled to an electric motor,
    sensing, via the at least one sensor, positional data and a direction of rotation of the electrical motor associated with pumping the fluid by the implantable device;
    and generating information indicative of a volume of fluid pumped by the implantable device based on the positional data and the direction of rotation.

12. The method of claim 11, wherein sensing the positional data and the direction of rotation comprises sensing using at least one hall effect sensor within the implantable device.

13. The method of claim 11, further comprising generating information indicative of a flow rate of the fluid pumped by the implantable device.

14. The method of claim 11, further comprising generating information indicative a viscosity of the fluid pumped by the implantable device.

15. The method of claim 11, wherein pumping the fluid from the first cavity comprises pumping the fluid through the inflow catheter in fluid communication with one of the following: a peritoneal cavity, a pleural cavity, or a pericardial cavity.

16. The method of claim 11, wherein pumping the fluid to the second cavity comprises pumping the fluid through the outflow catheter in fluid communication with a bladder or a peritoneal cavity.

17. The method of claim 11, further comprising charging, via an external charging and communication system, the implantable device.

18. The method of claim 17, further comprising communicating the information indicative of the volume of fluid pumped by the implantable device to the charging and communication system.

19. The method of claim 11, further comprising displaying, using monitoring and control software, the volume of fluid pumped based on the information indicative of the volume of fluid pumped by the implantable device.

* * * * *

UNITED STATES PATENT AND TRADEMARK OFFICE
CERTIFICATE OF CORRECTION

PATENT NO. : 11,235,131 B2
APPLICATION NO. : 16/378376
DATED : February 1, 2022
INVENTOR(S) : Thomas Werner Degen, Daniel Thomas Thommen and Noel L. Johnson It is certified that error appears in the above-identified patent and that said Letters Patent is hereby corrected as shown below:

On the Title Page

Under APPLICANTS, item (71), Line 2:
Delete "Lorraine Johnson"

Signed and Sealed this
Eighteenth Day of October, 2022

Katherine Kelly Vidal
*Director of the United States Patent and Trademark Office*